United States Patent
Yin et al.

(10) Patent No.: US 12,037,396 B2
(45) Date of Patent: Jul. 16, 2024

(54) HUMANIZED ANTI-HUMAN CTLA4 MONOCLONAL ANTIBODY, PREPARATION METHOD THEREFOR AND USE THEREOF

(71) Applicant: Nanjing GenScript Biotech Co., Ltd., Jiangsu (CN)

(72) Inventors: Liusong Yin, Jiangsu (CN); Tielin Zhou, Singapore (SG); Zhuo Fang, Jiangsu (CN); Yanling Mi, Jiangsu (CN); Chunchen Wu, Jiangsu (CN)

(73) Assignee: Nanjing GenScript Biotech Co., Ltd., Jiangsu (CN)

( * ) Notice: Subject to any disclaimer, the term of this patent is extended or adjusted under 35 U.S.C. 154(b) by 171 days.

(21) Appl. No.: 17/263,148

(22) PCT Filed: Jul. 25, 2019

(86) PCT No.: PCT/CN2019/097643
§ 371 (c)(1),
(2) Date: Jan. 25, 2021

(87) PCT Pub. No.: WO2020/020275
PCT Pub. Date: Jan. 30, 2020

(65) Prior Publication Data
US 2021/0301021 A1 Sep. 30, 2021

(30) Foreign Application Priority Data
Jul. 25, 2018 (CN) .......................... 201810828835.4

(51) Int. Cl.
*C07K 16/28* (2006.01)
(52) U.S. Cl.
CPC ...... *C07K 16/2818* (2013.01); *C07K 2317/24* (2013.01); *C07K 2317/92* (2013.01)
(58) Field of Classification Search
CPC ............ C07K 16/2818; C07K 2317/24; C07K 2317/09
See application file for complete search history.

(56) References Cited

U.S. PATENT DOCUMENTS

| | | | |
|---|---|---|---|
| 2014/0105914 A1* | 4/2014 | Jones .................. | A61P 37/00 536/23.53 |
| 2016/0237154 A1* | 8/2016 | Gray .................... | A61P 37/00 |
| 2018/0118836 A1* | 5/2018 | Bernett ............... | C07K 16/2803 |

FOREIGN PATENT DOCUMENTS

| | | |
|---|---|---|
| CN | 108218987 A | 6/2018 |
| EP | 1 013 761 A2 | 6/2000 |
| EP | 1 013 761 A3 | 11/2004 |
| WO | WO 2012/120125 A1 | 9/2012 |

OTHER PUBLICATIONS

Hall, B L et al. "A single amino acid mutation in CDR3 of the 3-14-9 L chain abolished expression of the IDA 10-defined idiotope and antigen binding." Journal of immunology (Baltimore, MD. : 1950) vol. 149,5 (1992): 1605-12. (Year: 1992) (Year: 1992).*
Rabia, Lilia A et al. "Understanding and overcoming trade-offs between antibody affinity, specificity, stability and solubility." Biochemical engineering journal vol. 137 (2018): 365-374. doi: 10.1016/j.bej.2018.06.003. Epub Jun. 5, 2018. (Year: 2018) (Year: 2018).*
Jirholt, P., Ohlin, M., Borrebaeck, C.A.K. & Söderlind, E. Exploiting sequence space: shuffling in vivo formed complementarity determining regions into a master framework. Gene 215, 471-476 (1998). (Year: 1998).*
Söderlind, E., Strandberg, L., Jirholt, P. et al. Recombining germline-derived CDR sequences for creating diverse single-framework antibody libraries. Nat Biotechnol 18, 852-856 (2000). https://doi.org/10.1038/78458 (Year: 2000).*
CDR Annotation. Novolabs. Accessed Dec. 18, 2023. https://www.novoprolabs.com/tools/cdr (Year: 2023).*
PCT/CN2019/097643 International Search Report and Written Opinion mailed on Oct. 25, 2019 (10 pages).
PCT/CN2019/097643 English translation of International Search Report mailed on Oct. 25, 2019 (4 pages).
Extended European Search Report dated Mar. 25, 2022 in European Application No. 19841732.1 (13 pages).
Kabat and Wu, "Identical V Region Amino Acid Sequences and Segments of Sequences in Antibodies of Different Specificities," *J Immunol.* 147:1709-1719, 1991.
Kuramochi et al., "Humanization and Simultaneous Optimization of Monoclonal Antibody," in *Human Monoclonal Antibodies: Methods and Protocols, Methods Mol Biol.*, Michael Steinitz (ed.), vol. 1060, pp. 123-137, Springer Science+Business Media, LLC, 2014.
Winter and Harris, "Humanized Antibodies," *Immunol. Today* 14:243-246, 1993.

* cited by examiner

*Primary Examiner* — Kevin S Orwig
*Assistant Examiner* — Lea S O'Brien
(74) *Attorney, Agent, or Firm* — Klarquist Sparkman, LLP

(57) ABSTRACT

The present invention relates to a humanized anti-human CTLA4 monoclonal antibody. The present invention also relates to a preparation method and application of the humanized anti-human CTLA4 monoclonal antibody.

19 Claims, 26 Drawing Sheets
Specification includes a Sequence Listing.

HUMANIZED ANTI-HUMAN CTLA4 MONOCLONAL ANTIBODY, PREPARATION METHOD THEREFOR AND USE THEREOF

CROSS REFERENCE TO RELATED APPLICATIONS

This is the U.S. National Stage of International Application No. PCT/CN2019/097643, filed Jul. 25, 2019, which was published in Chinese under PCT Article 21(2), which in turn claims the benefit of Chinese Patent Application No. 201810828835.4, filed Jul. 25, 2018.

INCORPORATION OF ELECTRONIC SEQUENCE LISTING

The electronic sequence listing, submitted herewith as a txt file named sequence listing.txt (28,672 bytes), created on Jun. 30, 2023, is herein incorporated by reference in its entirety.

BACKGROUND

Technical Field

The present invention belongs to the field of tumor immunotherapy and molecular immunology, and particularly relates to a humanized anti-human CTLA4 monoclonal antibody. The present invention also relates to a preparation method and application of the humanized anti-human CTLA4 monoclonal antibody.

RELATED ART

The vertebrate immune system is a functional system consisting of a variety of organs, tissues, cells and molecules, which is the most effective mechanism for the body to defend against foreign invasion (Janeway et al., Immunology: The Immune System in Health and Disease. New York: Garland Science, 2005). Immune organs, tissues and cells cooperate and balance each other. Under the coordination of many immune checkpoint proteins and cytokines, the effects of protecting the body from external infection and maintaining homeostasis are achieved. An acquired immune system against foreign pathogens consists of humoral immunity (mediated by B cells) and cellular immunity (mediated by T cells). Cellular immunity is caused by the recognition of an antigen presented by a major histocompatibility complex (MHC) on an antigen presenting cell (APC) by a T cell receptor (TCR). This activation also requires costimulation of APC. The two homologous B7 family members B7-1 (also called B7, B7.1 or CD80) and B7-2 (also called B7.2 or CD86) on the APC can both deliver co-stimulatory signals when binding to the CD28 antigen on T cells, leading to T cell activation. Both CTLA4 and CD28 are members of the Ig superfamily containing a single extracellular Ig domain and both can bind to the B7 protein, but the regulatory effects are opposite. CTLA4 has a higher affinity than CD28 when binding to the B7 protein and competes to form a more stable interaction, which makes T cells lack second-level stimulating signals and become anergic; at the same time, T cell apoptosis can be induced after T cell activation. In this way, the immune system is negatively regulated, and the homeostasis of T cells in the body is maintained. Therefore, blocking negative regulatory signals conducted by CTLA4 with monoclonal antibodies can provide new therapies for human diseases which benefit from immune stimulation, such as immunotherapy for cancer and infectious diseases. Currently, a CTLA4 monoclonal antibody has been used in different clinical trial stages to treat a variety of human cancers, including melanoma, prostate cancer, bladder cancer, colorectal cancer, malignant mesothelioma, gastrointestinal cancer, liver cancer and non-small cell lung cancer (Grosso et al., Cancer Immunology 13:5, 2013). Ipilimumab (Keler et al., J Immunol 171:6251-6259 (2003)) and Tremelimumab (Ribas et al., Oncologist 12:873-883 (2005)) are now available. A CTLA4 monoclonal antibody that has been successfully marketed, Ipilimumab (trade name Yervoy), indicates that tumor immunotherapy is feasible in the clinical stage. Moreover, as preclinical experiments have verified the ability of monoclonal antibodies against different immunomodulatory factors in the synergistic treatment of cancer, the CTLA4 monoclonal antibody has formed a combination therapy with monoclonal antibodies of different immunosuppressive molecules or small molecule compounds, and clinical trials on different cancers is carried out. However, there is only one CTLA4 monoclonal antibody currently on the market, and the CTLA4 monoclonal antibody also has different degrees of side effects, including induction of immunogenicity in some patients, excessive suppression of CTLA4 signals may cause autoimmune diseases, and different CTLA4 monoclonal antibodies have different degrees of developability. At the same time, in order to avoid differences in the efficacy of different patient populations, the development of new humanized functional antibodies which have higher affinity, specificity, functionality and diversity and can block the binding of CTLA4 and B7 protein has become an urgent problem to be solved in tumor immunotherapy.

SUMMARY

In one aspect, the present invention provides a humanized anti-human CTLA4 monoclonal antibody or a functional fragment thereof, comprising a heavy chain variable region and a light chain variable region, the heavy chain variable region comprises amino acid sequences having at least 80% identity with the following HCDR1, HCDR2 and HCDR3 sequences respectively, and the light chain variable region comprises amino acid sequences having at least 80% identity with the following LCDR1, LCDR2 and LCDR3 sequences respectively:

the amino acid sequence of HCDR1 is

```
                                        (SEQ ID NO: 25)
        SYWIN;
``` the amino acid sequence of HCDR2 is

```
                                        (SEQ ID NO: 26)
        RIAPGSGTTYYNEMFTG;
``` the amino acid sequence of HCDR3 is

```
                                        (SEQ ID NO: 27)
        GDYFDY;
``` the amino acid sequence of LCDR1 is

```
                                        (SEQ ID NO: 28)
        SASKSVSYIH;
``` the amino acid sequence of LCDR2 is

```
                                           (SEQ ID NO: 29)
             DTSTLAS;
```
and
the amino acid sequence of LCDR3 is

```
                                           (SEQ ID NO: 30)
             QQRTTYPLT;
```

In an embodiment, the heavy chain variable region comprises amino acid sequences having at least 70%, at least 80%, at least 85%, at least 90% or at least 95% identity with the HCDR1, HCDR2 and HCDR3 sequences respectively.

In an embodiment, the light chain variable region comprises amino acid sequences having at least 70%, at least 80%, at least 85%, at least 90% or at least 95% identity with the following LCDR1, LCDR2 and LCDR3 sequences respectively.

In an embodiment, the present invention provides a humanized anti-human CTLA4 monoclonal antibody or a functional fragment thereof, comprising a heavy chain variable region and a light chain variable region, the heavy chain variable region comprises amino acid sequences shown as the following HCDR1, HCDR2 and HCDR3 sequences, and the light chain variable region comprises amino acid sequences shown as the following LCDR1, LCDR2 and LCDR3 sequences:

the amino acid sequence of HCDR1 is

```
                                           (SEQ ID NO: 25)
             SYWIN;
```
the amino acid sequence of HCDR2 is

```
                                           (SEQ ID NO: 26)
             RIAPGSGTTYYNEMFTG;
```
the amino acid sequence of HCDR3 is

```
                                           (SEQ ID NO: 27)
             GDYFDY;
```
the amino acid sequence of LCDR1 is

```
                                           (SEQ ID NO: 28)
             SASKSVSYIH;
```
the amino acid sequence of LCDR2 is

```
                                           (SEQ ID NO: 29)
             DTSTLAS;
```
and
the amino acid sequence of LCDR3 is

```
                                           (SEQ ID NO: 30)
             QQRTTYPLT.
```

The present invention provides a humanized anti-human CTLA4 monoclonal antibody or a functional fragment thereof, comprising a heavy chain variable region and a light chain variable region, the heavy chain variable region comprises amino acid sequences in which one, two or three amino acid residues are substituted, inserted or deleted in the following HCDR1, HCDR2 and HCDR3 sequences respectively, and the light chain variable region comprises amino acid sequences in which one, two or three amino acid residues are substituted, inserted or deleted in the following LCDR1, LCDR2 and LCDR3 sequences respectively:

the amino acid sequence of HCDR1 is

```
                                           (SEQ ID NO: 25)
             SYWIN;
```
the amino acid sequence of HCDR2 is

```
                                           (SEQ ID NO: 26)
             RIAPGSGTTYYNEMFTG;
```
the amino acid sequence of HCDR3 is

```
                                           (SEQ ID NO: 27)
             GDYFDY;
```
the amino acid sequence of LCDR1 is

```
                                           (SEQ ID NO: 28)
             SASKSVSYIH;
```
the amino acid sequence of LCDR2 is

```
                                           (SEQ ID NO: 29)
             DTSTLAS;
```
and
the amino acid sequence of LCDR3 is

```
                                           (SEQ ID NO: 30)
             QQRTTYPLT.
```

In an embodiment, the amino acid sequence of the heavy chain variable region is selected from SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16.

In an embodiment, the amino acid sequence of the light chain variable region is selected from SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24.

In an embodiment, wherein
the heavy chain variable region is SEQ ID NO: 9 and the light chain variable region is SEQ ID NO: 17;
the heavy chain variable region is SEQ ID NO: 10 and the light chain variable region is SEQ ID NO: 18;
the heavy chain variable region is SEQ ID NO: 11 and the light chain variable region is SEQ ID NO: 19;
the heavy chain variable region is SEQ ID NO: 12 and the light chain variable region is SEQ ID NO: 20;
the heavy chain variable region is SEQ ID NO: 13 and the light chain variable region is SEQ ID NO: 21;
the heavy chain variable region is SEQ ID NO: 14 and the light chain variable region is SEQ ID NO: 22;
the heavy chain variable region is SEQ ID NO: 15 and the light chain variable region is SEQ ID NO: 23; or
the heavy chain variable region is SEQ ID NO: 16 and the light chain variable region is SEQ ID NO: 24.

In an embodiment, wherein
the heavy chain variable region is SEQ ID NO: 10 and the light chain variable region is SEQ ID NO: 18;

the heavy chain variable region is SEQ ID NO: 11 and the light chain variable region is SEQ ID NO: 19;
the heavy chain variable region is SEQ ID NO: 12 and the light chain variable region is SEQ ID NO: 20; or
the heavy chain variable region is SEQ ID NO: 14 and the light chain variable region is SEQ ID NO: 22.

In an embodiment, wherein
the heavy chain variable region is SEQ ID NO: 11 and the light chain variable region is SEQ ID NO: 19; or
the heavy chain variable region is SEQ ID NO: 14 and the light chain variable region is SEQ ID NO: 22.

In an embodiment, the humanized anti-human CTLA4 monoclonal antibody or a functional fragment thereof of the present invention comprises a heavy chain having an amino acid sequence shown as SEQ ID NO: 1 and a light chain having an amino acid sequence shown as SEQ ID NO: 2.

In an embodiment, a dissociation constant KD between the humanized anti-human CTLA4 monoclonal antibody or a functional fragment thereof and CLTA4 is lower than 0.02 nM.

In an embodiment, the humanized anti-human CTLA4 monoclonal antibody or a functional fragment thereof of the present invention specifically relieves the negative immune regulation of CTLA4 and activates T cells to secrete cytokines.

In another aspect, the present invention provides an isolated polynucleotide encoding the humanized anti-human CTLA4 monoclonal antibody or a functional fragment thereof.

In an embodiment, the polynucleotide of the present invention comprises a heavy chain coding sequence encoding the heavy chain variable region of the humanized anti-human CTLA4 monoclonal antibody and a light chain coding sequence encoding the light chain variable region of the humanized anti-human CTLA4 monoclonal antibody.

In another aspect, the present invention provides an expression vector comprising the polynucleotide.

In another aspect, the present invention provides a host cell comprising the expression vector.

In an embodiment, the host cell is a HEK293-6E cell.

In another aspect, the present invention provides application of the humanized anti-human CTLA4 monoclonal antibody or a functional fragment thereof, the polynucleotide, the expression vector or the host cell in preparation of anti-tumor drugs.

In another aspect, the present invention provides application of the humanized anti-human CTLA4 monoclonal antibody or a functional fragment thereof, the polynucleotide, the expression vector or the host cell in treatment of tumors.

In an embodiment, the tumors are selected from multiple myeloma, non-small cell lung cancer, colorectal cancer, renal cell carcinoma, prostate cancer, breast cancer and ovarian cancer.

In another aspect, the humanized anti-human CTLA4 monoclonal antibody or a functional fragment thereof, the polynucleotide, the expression vector or the host cell provided in the present invention are used for treating tumors.

In an embodiment, the tumors are selected from multiple myeloma, non-small cell lung cancer, colorectal cancer, renal cell carcinoma, prostate cancer, breast cancer and ovarian cancer.

In another aspect, the present invention provides an anti-tumor pharmaceutical composition comprising an effective amount of the humanized anti-human CTLA4 monoclonal antibody or a functional fragment thereof and a pharmaceutically acceptable carrier.

In another aspect, the present invention provides a method for preparing the humanized anti-human CTLA4 monoclonal antibody or a functional fragment thereof, comprising transfecting competent cells with an expression vector and culturing the cells.

In another aspect, the present invention provides a method for preparing the humanized anti-human CTLA4 monoclonal antibody or a functional fragment thereof, comprising:
(1) humanizing a mouse-derived antibody to obtain variable region coding sequences of a light chain and a heavy chain of the humanized anti-human CTLA4 monoclonal antibody or a functional fragment thereof; and
(2) performing recombinant antibody production by using the variable region coding sequences, so as to obtain the functional humanized anti-human CTLA4 monoclonal antibody or a functional fragment thereof.

The humanized anti-human CTLA4 monoclonal antibody provided by the present invention has high affinity and high specificity for CTLA4, and can stimulate T cells to secrete cytokines, such as specifically relieve the negative immune regulation of CTLA4 and activate T cells to secrete cytokines. Therefore, the functional humanized anti-human CTLA4 monoclonal antibody provided by the present invention can activate T cells by blocking a CTLA4 signal pathway, thereby achieving the purpose of tumor immunotherapy.

BRIEF DESCRIPTION OF THE DRAWINGS

(FIG. 7C), AH01674-AAPH (FIG. 7D), AH01695 (FIG. 7E) and AH01695-AAPH (FIG. 7F).

DETAILED DESCRIPTION

Figure 1A:
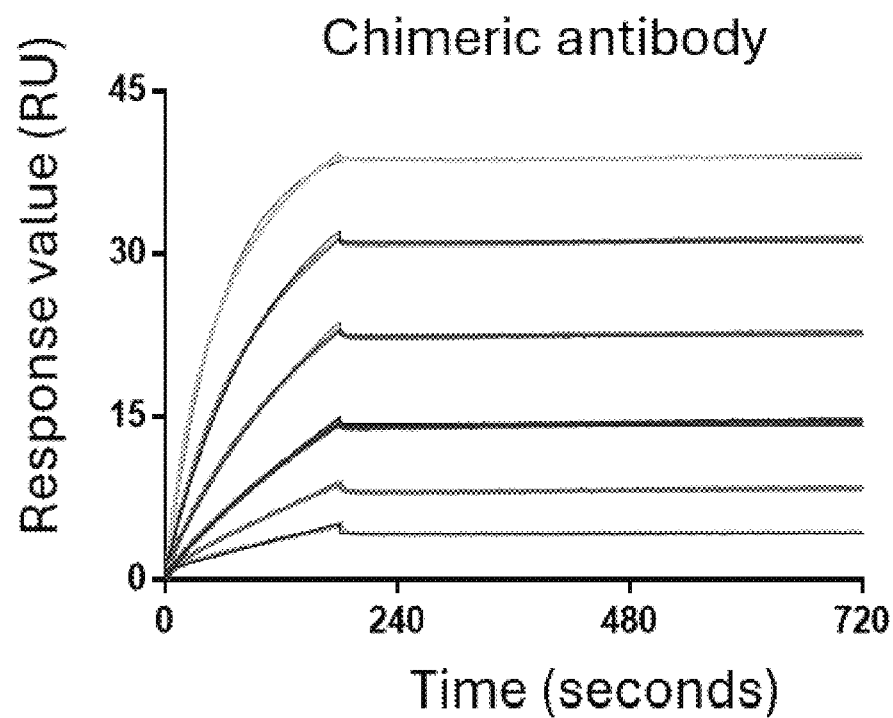
FIGS. 1A-1H show affinity measurement of humanized anti-human CTLA4 monoclonal antibodies.

Unless otherwise specified, the technical and scientific terms used in the present invention have the meanings commonly understood by those skilled in the art to which the present invention belongs.

As used herein, the term "antibody" refers to an immunoglobulin molecule, which is usually a tetramer consisting of two identical heavy chains and two identical light chains connected to each other by disulfide bonds. According to conservative differences in amino acid sequences, the heavy chain and the light chain are divided into a variable region (V) at the amino terminal and a constant region (C) at the carboxy terminal. In the variable regions of the heavy chain and the light chain, there are three partial regions with a higher degree of variation in the amino acid composition and arrangement order, which are the key positions for the antibody to bind to the antigen, and such region is also called a complementary determining region (CDR). Herein, the three heavy chain complementary determining regions are called HCDR1, HCDR2 and HCDR3 respectively, and the three light chain complementary determining regions are called LCDR1, LCDR2 and LCDR3 respectively. The variable regions of a heavy chain and a light chain interact to form an antigen binding site (Fv). According to amino acid sequences of the heavy chain constant regions, antibodies can be divided into different classes. There are five main types of intact antibodies: IgA, IgD, IgE, IgG and IgM, and some of these antibodies can be further divided into subclasses, for example, IgG1, IgG2, IgG3, IgG4, IgA1 and IgA2. The subunit structures and three-dimensional conformations of different classes of immunoglobulins are known in the art. The present invention is intended to include antibodies of any of the classes or subclasses.

As used herein, the term "antibody" is also intended to cover digested fragments or functional variants thereof, for example, antibody fragments capable of binding to CTLA4 or a part thereof, including but not limited to Fab (such as antibodies obtained by papain digestion), F(ab')2 (such as antibodies obtained by pepsin digestion) and Fv or scFv (such as antibodies obtained by molecular biology techniques).

As used herein, the term "monoclonal antibody" refers to a uniform antibody that only targets a specific epitope. Compared with ordinary polyclonal antibody preparations which typically include different antibodies against different antigenic determinants (epitopes), each monoclonal antibody is directed against a single antigenic determinant on an antigen.

The modifier "monoclonal" refers to the uniform characteristics of an antibody, and is not interpreted as an antibody that needs to be produced by any specific method. The monoclonal antibodies of the present invention are preferably produced by a DNA recombination method or obtained by a screening method described elsewhere herein.

As used herein, the term "isolated polynucleotide" refers to a polynucleotide that does not occur naturally in nature, including polynucleotides isolated from nature (including organisms) through biological techniques and artificially synthesized polynucleotides. The isolated polynucleotide may be genomic DNA, cDNA, mRNA or other synthetic RNA, or a combination thereof. Herein provided is a number of nucleotide sequences encoding the heavy chain variable region and the light chain variable region of a humanized anti-CTLA4 monoclonal antibody. It should be noted that those skilled in the art can design nucleotide sequences that are not completely identical to the nucleotide sequences provided above, but both encode the same amino acid sequence according to the amino acid sequences of the heavy chain variable region and the light chain variable region provided herein on the basis of codon degeneracy. These modified nucleotide sequences are also included in the scope of the present invention.

As used herein, the "modification" of an amino acid residue/position refers to a primary amino acid sequence change relative to an original amino acid sequence, wherein the change comes from a change in the sequence involving an amino acid residue/position. For example, typical modifications include substituting (such as conservative or non-conservative substitution) a residue (at the position) with another amino acid, inserting one or more (generally less than 5 or 3) amino acids into a position adjacent to the residue/position and deleting the residue/position. "Amino acid substitution" or a change thereof refers to substitution of an existing amino acid residue with different amino acid residues in a predetermined (original) amino acid sequence. Relative to a polypeptide containing an original (or "wild-type") amino acid sequence, the modification generally preferably produces at least one physiological and biochemical activity change of a variant polypeptide. For example, for antibodies, the changed physiological and biochemical activity may be the binding affinity, binding capacity and/or binding effect for a target molecule.

The "percent (%) amino acid sequence identity" of a peptide or polypeptide sequence is defined as the percentage of amino acid residues in a candidate sequence identical to the amino acid residues in a specific peptide or polypeptide sequence after the sequences are compared and gaps are introduced when necessary to obtain the maximum percent sequence identity without considering any conservative substitutions as part of the sequence identity. Sequence comparison can be performed in a variety of ways within the skill of the art to determine percent amino acid sequence identity, for example, publicly available computer software such as BLAST, BLAST-2, ALIGN or Megalign (DNASTAR) software is used. Those skilled in the art can determine appropriate parameters for measuring the comparison, including any algorithm required to obtain the maximum comparison over the entire length of the sequences being compared.

When referring to polynucleotide, the term "vector" as used herein refers to any molecule (such as nucleic acid, plasmid or virus) used to transfer nucleotide coding information into a host cell. The term "expression vector" or "expression cassette" refers to a vector suitable for expressing a target gene (nucleotide sequence to be expressed) in a host cell, and usually includes a target gene, a promoter, a terminator, a marker gene and other parts.

The term "host cell" as used herein refers to a cell that has been or is capable of being transformed with a nucleic acid sequence and thereby expressing a selected target gene. The term includes the offspring of a parent cell, regardless of whether the offspring and the original parent cell are the same in morphology or genetic composition, as long as the offspring has the selected target gene. Commonly used host cells include bacteria, yeast, mammalian cells and the like.

The term "transfection" as used herein refers to the uptake of foreign or exogenous DNA by cells, and this technique can be used to introduce one or more foreign DNA portions into a suitable host cell. Physical and chemical methods (such as calcium chloride treatment) can be used to induce cells to stay in a physiological state that is optimal for ingesting and accommodating foreign DNA, that is, "competence".

When referring to a pharmaceutical composition, the term "effective amount" as used herein refers to an amount that can produce function or activity on humans and/or animals and can be accepted by humans and/or animals. "Pharmaceutically acceptable carrier" refers to a carrier for administration, including various excipients, diluents, buffers and the like. These substances are suitable for administration to humans and/or animals without excessive side effects, and at the same time, the substances are suitable for maintaining the vitality of the drugs or active agents therein.

Some aspects of the present invention will be described in detail below in conjunction with specific examples. Unless otherwise specified, the methods and materials in the examples described below are commercially available and conventional products.

EXAMPLES

Example 1 Humanization of a Mouse-Derived Anti-Human CTLA4 Antibody

1) A 42B11G12D3 antibody sequence of a mouse-derived anti-human CTLA4 antibody (CDR regions are underlined) (see, for example, SEQ ID NOs: 1-2)

```
SEQ ID NO: 1, 42B11G12D3-VH
QVHLQQSGDVLVKPGASVNLSCKASGYTFTSYWINWIKQRPGQGLEWIG
RIAPGSGTTYYNEMFTGKATLTVVISSTTAYIQLSSLSFEDSAVYFCAR
GDYFDYWDQGTTLTVSS

SEQ ID NO: 2, 42B11G12D3-VL
QIVLTQSPAIMSASPGGKVTITCSASKSVSYIHWFQQKPGTSPKLLIYD
ISTLASGVPPRFSGSGSGPSYSLTISRMEAEDAATYYCQQRTTYPLTFG
GGTKLEVR
```

2) Construction of a CDR-grafted plasmid of an anti-human CTLA4 antibody

An IMGT human V gene (F+ORF+in-frameP) database was selected, a human Germline antibody sequence with the highest homology was selected as a humanized receiving vector based on comparison, three heavy chain complementary determining regions HCDR1, HCDR2 and HCDR3 and three light chain complementary determining regions LCDR1, LCDR2 and LCDR3 in the mouse antibody were transferred to corresponding positions, and post-translational modification sites (PTM) were analyzed, see Table 1. Sequence analysis showed that the two sites W33 and M63 were hot spots for post-translational oxidation modification (see, for example, SEQ ID NOs: 3-4).

```
SEQ ID NO: 3, 42B11G12D3-VH-GRAFTED
QVQLVQSGAEVKKPGASVKVSCKASGYTFTSYWINWVRQAPGQGLEWMG
RIAPGSGTTYYNEMFTGRVTMTRDTSISTVYMELSSLRSEDTAVYYCAI
GDYFDYWGQGTMVTVSS

SEQ ID NO: 4, 42B11G12D3-VL-GRAFTED
DIQLTQSPSFLSASVGDRVTITCSASKSVSYIHWYQQKPGKAPKLLIYD
TSTLASGVPSRFSGSGSGTEFTLTISSLOPEDFATYYCQQRTTYPLTFG
QGTKLEIK
```

TABLE 1

PTM risk analysis

| | M2-42B11G12D3 | |
|---|---|---|
| | VH | VL |
| Homology with human germline (%) | 60.2 IGHV1-46*01 | 64.9 IGKV1-9*01 |
| Extra cysteine | No | No |
| N-glycosylation | No | No |
| Asparagine deamidation | No | No |
| Aspartic acid isomerization | No | No |
| Oxidation | W33 M63 | No |
| Hydrolysis | No | No |

3) Design of a phage library CBM (grey shading), 5BM (bold), construction of Phage-Fab and FASEBA-Fab plasmids of an anti-human CTLA4 antibody 42B11G12D3 VH-VL, and screening of humanized antibody back mutation sites (see, for example, SEQ ID NOs: 5-8).

42B11G12D3_CBM

```
SEQ ID NO: 5, 42B11G12D3-VH-CBM
QVQLVQSGAEVKPGASVKSCKASGYTFTSYWINWQAPGQGLEWGR
IAPGSGTTYYNEMFTGRVTTRDISTSTTELSSLRSEDTAVCA
GDYFDYWQGTMVTVSS

SEQ ID NO: 6, 42B11G12D3-VL-CBM
DIQLTQSPSFLSASVGDRVTITCSASKSVSYIHWQQKPGKPKLLIYD
TSTLASGVPSRFSGSGSGTETLTISSQPEDFATYYCQQRTTYPLTFG
QGTKLEIK
```

42B11G12D3_5BM

```
SEQ ID NO: 7, 42B11G12D3-VH-5BM
QVHLVQSGAEVKKPGASVKVSCKASGYTFTSYWINWIKQAPGQGLEWIG
RIAPGSGTTYYNEMFTGRVTMTVVISTSTAYMELSSLRSEDTAVYYCAR
GDYFDYWDQGTMVTVSS

SEQ ID NO: 8, 42B11G12D3-VL-5BM
DIVLTQSPSFLSASVGDRVTITCSASKSVSYIHWYQQKPGKAPKLLIYD
TSTLASGVPPRFSGSGSGPSYSLTISSLOPEDFATYYCQQRTTYPLTFG
GGTKLEIK
```

4) Affinity ranking of prokaryotic expression antibody products and VH/VL sequences thereof (Table 2), and selection of sequences with the highest anti-human CTLA4 antibody affinity for eukaryotic system expression.

TABLE 2

Humanized back mutation screening of monoclonal antibodies and affinity ranking of antibodies with the highest affinity

|     |         | Analyte 1 solution | Kinetics Chi$^2$ (RU$^2$) | ka       | kd       | K$_D$ (M) | Rmax  | tc       | Kinetic model |
| --- | ------- | ------------------ | ------------------------- | -------- | -------- | --------- | ----- | -------- | ------------- |
| CBM | AH01653 | CTLA4/Fc           | 1.06E+01                  | 6.70E+05 | 1.00E−05 | 1.49E−11  | 105.1 | 5.18E+09 | 1:1 binding   |
|     | AH01672 | CTLA4/Fc           | 1.05E+01                  | 6.90E+05 | 1.00E−05 | 1.45E−11  | 104.9 | 2.68E+09 | 1:1 binding   |
|     | AH01674 | CTLA4/Fc           | 3.36E+01                  | 6.48E+05 | 1.00E−05 | 1.54E−11  | 207.2 | 3.32E+10 | 1:1 binding   |
| 5BM | AH01679 | CTLA4/Fc           | 3.08E+01                  | 9.47E+05 | 4.08E−08 | 4.31E−14  | 282.2 | 4.82E+09 | 1:1 binding   |
|     | AH01686 | CTLA4/Fc           | 2.57E+01                  | 9.17E+05 | 3.97E−08 | 4.33E−14  | 224   | 2.41E+09 | 1:1 binding   |
|     | AH01695 | CTLA4/Fc           | 2.18E+01                  | 8.13E+05 | 8.59E−09 | 1.06E−14  | 232.3 | 2.36E+10 | 1:1 binding   |
|     | AH01696 | CTLA4/Fc           | 4.53E+01                  | 7.97E+05 | 2.97E−09 | 3.73E−15  | 332.6 | 1.46E+09 | 1:1 binding   |
|     | AH01704 | CTLA4/Fc           | 2.45E+02                  | 4.38E+07 | 8.31E−07 | 1.90E−14  | 134.1 | 1.60E+09 | 1:1 binding   |

3 CBMs and 5 5BMs antibody sequences showing the highest affinity are as follows (see, for example, SEQ ID NOs: 9-24):

SEQ ID NO: 9, AH01653-VH
QVHLVQSGAEVKKPGASVKVSCKASGYTFTSYWINWVKQAPGQGLEWMG
RIAPGSGTTYYNEMFTGRVTMTRDTSTSTAYMELSSLRSEDTAVYYCAR
GDYFDYWDQGTMVTVSS

SEQ ID NO: 10, AH01672-VH
QVQLVQSGAEVKKPGASVKVSCKASGYTFTSYWINWVKQAPGQGLEWMG
RIAPGSGTTYYNEMFTGRVTMTRDTSTSTAYMELSSLRSEDTAVYYCAR
GDYFDYWDQGTMVTVSS

SEQ ID NO: 11, AH01674-VH
QVQLVQSGAEVKKPGASVKVSCKASGYTFTSYWINWVRQAPGQGLEWMG
RIAPGSGTTYYNEMFTGRVTMTRDTSTSTAYMELSSLRSEDTAVYYCAR
GDYFDYWGQGTMVTVSS

SEQ ID NO: 12, AH01679-VH
QVQLVQSGAEVVKPGASVKLSCKASGYTFTSYWINWVRQAPGQGLEWIG
RIAPGSGTTYYNEMFTGRVTMTRDTSTSTVYMELSSLRSEDTAVYYCAR
GDYFDYWGQGTMVTVSS

SEQ ID NO: 13, AH01686-VH
QVQLVQSGAEVVKPGASVKVSCKASGYTFTSYWINWIKQAPGQGLEWIG
RIAPGSGTTYYNEMFTGRVTLTRDTSTSTAYIELSSLRSEDTAVYFCAR
GDYFDYWGQGTMVTVSS

SEQ ID NO: 14, AH01695-VH
QVQLVQSGAEVKKPGASVKVSCKASGYTFTSYWINWVRQAPGQGLEWMG
RIAPGSGTTYYNEMFTGRVILTRDTSTSTAYIELSSLRSEDTAVYFCAI
GDYFDYWGQGTMVTVSS

SEQ ID NO:15, AH01696-VH
QVQLVQSGAEVVKPGASVKVSCKASGYTFTSYWINWIRQAPGQGLEWIG
RIAPGSGTTYYNEMFTGRVTLTRDISTSTAYMELSSLRSEDTAVYYCAR
GDYFDYWDQGTMVTVSS

SEQ ID NO: 16, AH01704-VH
QVQLVQSGAEVVKPGASVKVSCKASGYTFTSYWINWVKQAPGQGLEWMG
RIAPGSGTTYYNEMFTGRVTLTRDTSTSTAYMELSSLRSEDTAVYFCAR
GDYFDYWGQGTMVTVSS

SEQ ID NO: 17, AH01653-VL
DIQLTQSPSFLSASVGDRVTITCSASKSVSYIHWYQQKPGKAPKLLIYD
ISTLASGVPSRFSGSGSGPEYTLTISSLOPEDFATYYCQQRTTYPLTFG
GGTKLEIK

SEQ ID NO: 18, AH01672-VL
DIQLTQSPSFLSASVGDRVTITCSASKSVSYIHWYQQKPGKAPKLLIYD
TSTLASGVPPRFSGSGSGPEFSLTISSLQPEDFATYYCQQRTTYPLTFG
GGTKLEIK

SEQ ID NO: 19, AH01674-VL
DIQLTQSPSFLSASVGDRVTITCSASKSVSYIHWYQQKPGKAPKLLIYD
TSTLASGVPPRFSGSGSGPEFTLTISSLOPEDFATYYCQQRTTYPLTFG
QGTKLEIK

SEQ ID NO: 20, AH01679-VL
DIQLTQSPSFLSASVGDRVTITCSASKSVSYIHWYQQKPGKAPKLLIYD
ISTLASGVPSRFSGSGSGTEFTLTISSLOPEDFATYYCQQRTTYPLTFG
QGTKLEIK

SEQ ID NO: 21, AH01686-VL
DIQLTQSPSFLSASVGDRVTITCSASKSVSYIHWYQQKPGKAPKLLIYD
ISTLASGVPSRFSGSGSGTEFTLTISSLOPEDFATYYCQQRTTYPLTFG
QGTKLEIK

SEQ ID NO: 22, AH01695-VL
DIQLTQSPSFLSASVGDRVTITCSASKSVSYIHWYQQKPGKAPKLLIYD
TSTLASGVPSRFSGSGSGTEFTLTISSLOPEDFATYYCQQRTTYPLTFG
QGTKLEIK

SEQ ID NO: 23, AH01696-VL
DIQLTQSPSFLSASVGDRVTITCSASKSVSYIHWFQQKPGKAPKLLIYD
ISTLASGVPSRFSGSGSGTEYTLTISSLOPEDFATYYCQQRTTYPLTFG
QGTKLEIK

SEQ ID NO: 24, AH01704-VL
DIQLTQSPSFLSASVGDRVTITCSASKSVSYIHWYQQKPGKAPKLLIYD
TSTLASGVPSRFSGSGSGTEYTLTISSLOPEDFATYYCQQRTTYPLTFG
QGTKLEIK

Example 2: Recombinant Production of Humanized Antibodies

The selected antibody VH and VL sequences were subjected to codon optimization, ligated to a secretion signal peptide at the 5'end, then ligated to the human antibody IgG1 heavy chain and κ light chain constant region sequences and separately cloned into a pTT5 expression vector to prepare human antibody DNA sequences which could be expressed and secreted in mammalian cells. Plasmids were co-transfected with PEI into HEK293-6E suspension culture cells for transient expression. During transfection, the cell density was maintained at 1*10$^6$ cells/mL, and the PEI:DNA ratio was 3:1. The cells were subjected to shaking culture in a 5%

$CO_2$ incubator at 37° C. and 105 rpm/min. 24 hours after transfection, 0.5% Trypton N−1 was added. 5 days later, the cell culture supernatant was collected, antibodies were purified by using protein-A agarose gel and quantified, and the purity was identified (Table 3).

TABLE 3

Recombinant production of humanized antibodies

| Sample-ID | | | Antibody | Antibody | Total | Antibody |
|---|---|---|---|---|---|---|
| ID sequence | Clone number | Transfection system | concentration (mg/ml) | volume (ml) | antibody (mg) | purity (%) |
| AD15-3-5BM | AH01653 | 50 ml | 0.023 | 2.2 | 0.05 | 90% |
| AD15-3-5BM | AH01672 | 50 ml | 0.784 | 1.5 | 1.18 | 90% |
| AD15-3-5BM | AH1674 | 50 ml | 0.565 | 2.2 | 1.24 | 99% |
| AD15-3-CBM | AH01679 | 50 ml | 0.341 | 3.7 | 1.26 | 88% |
| AD15-3-CBM | AH01686 | 50 ml | 0.737 | 0.2 | 0.15 | 99% |
| AD15-3-CBM | AH01695 | 50 ml | 0.267 | 3.7 | 0.99 | 90% |
| AD15-3-CBM | AH01696 | 50 ml | 0.207 | 2.2 | 0.46 | 97% |
| AD15-3-CBM | AH01704 | 50 ml | 0.232 | 0.2 | 0.05 | 99% |

Example 3: Affinity Measurement of a Humanized Monoclonal Antibody

The surface of a chip was equilibrated with an HBS-EP buffer at a flow rate of 10 μl/min for 5 minutes, then a 1:1 mixture of NHS and EDC was injected at a flow rate of 10 μl/min for 7 minutes to activate the chip, a capture antibody (Goat anti-mouse IgG) diluted in a 10 mM sodium acetate buffer was injected at a flow rate of 10 l/min for about 7 minutes for coupling, and finally ethanolamine was injected at a flow rate of 10 μl/min for 7 minutes for surface blocking.

The HBS-EP buffer was used as a sample for three pre-circulations to balance the chip so as to stabilize the baseline, an antibody diluted in the HBS-EP buffer was injected at a flow rate of 10 μl/min for 0-5 minutes (a binding signal of an antibody and an antigen was controlled to be about 100 RU by adjusting the capture time), and the buffer was equilibrated for 1 minute. A low concentration antigen 0.33 nM CTLA4-Fc was injected at a flow rate of 30 μl/min for 5 minutes, the antigen bound to the antibody, then a buffer was injected at a flow rate of 30 μl/min for 15 minutes for dissociation, 50 mM HCl was injected at a flow rate of 100 μl/min four times involving regeneration in 10 seconds each time, and thus one cycle ended.

The antigen concentration was changed to perform the next gradient concentration of cycle measurement until all gradient concentration (1.25 nM, 2.5 nM, 5 nM, 10 nM, 20 nM, 40 nM) and repeated concentration (such as 5 nM CTLA4-Fc) measurements ended. After the experimental data was subjected to double subtraction (control channel and zero concentration), a "1:1 binding" model was fitted in the Biacore 8K evaluation software. Biacore 8K was used to measure the affinity of an antibody against the CTLA4-Fc recombinant protein.

Figure 1B:
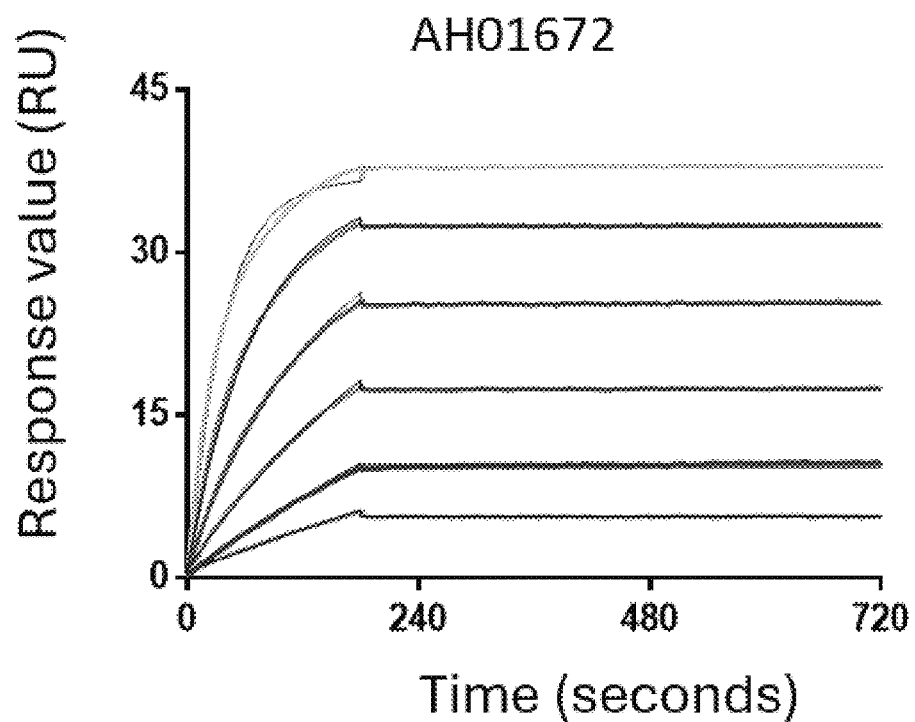
Figure 1C:
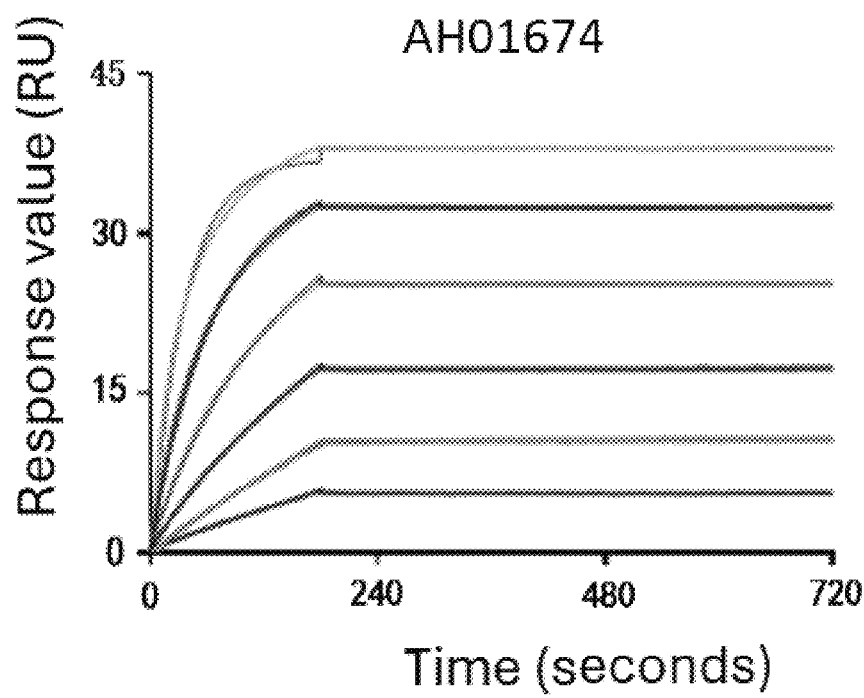
Figure 1D:
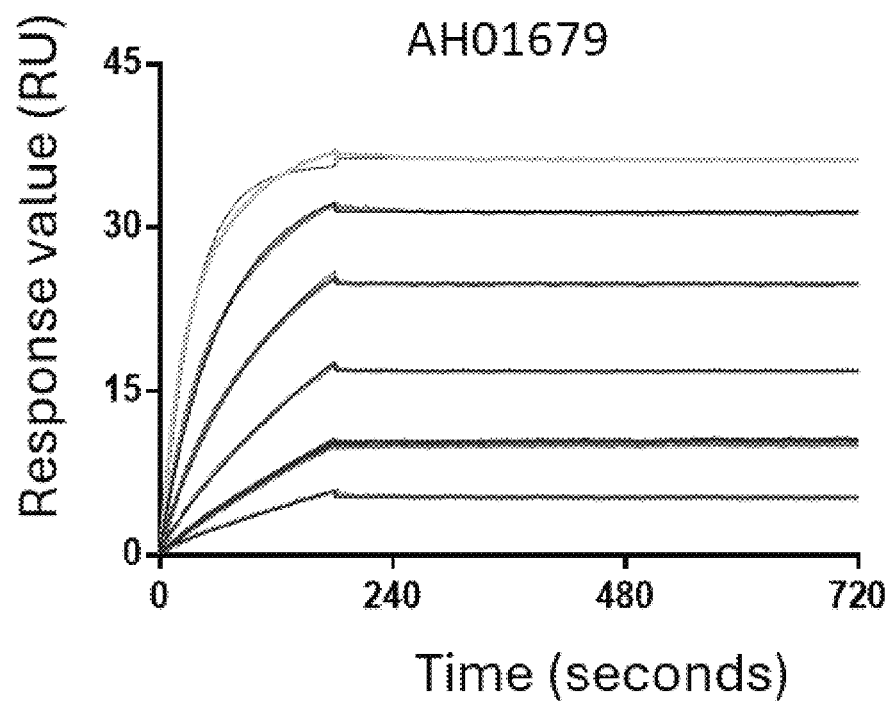
Figure 1E:
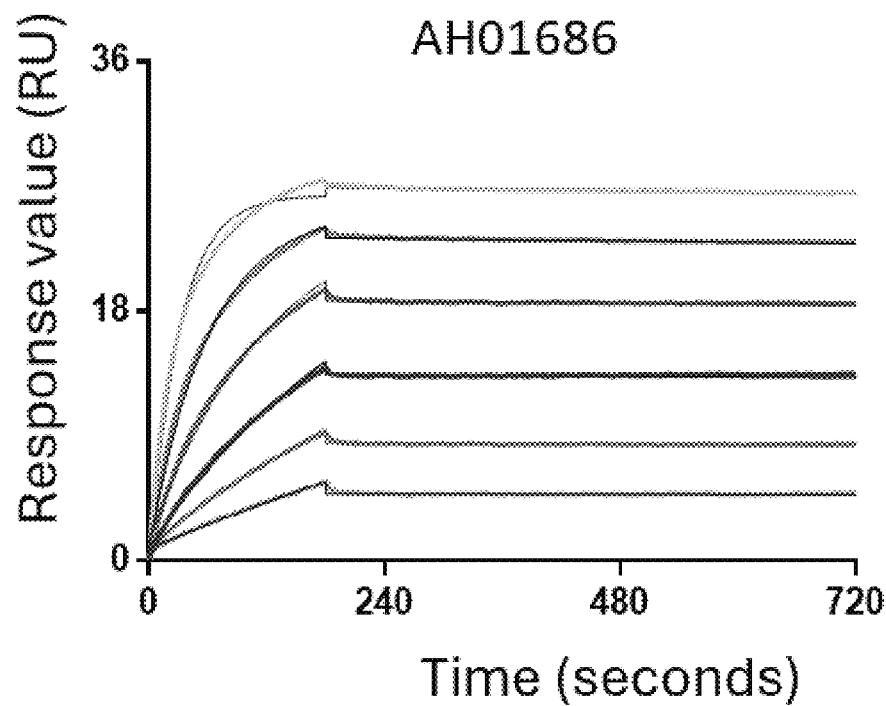
Figure 1F:
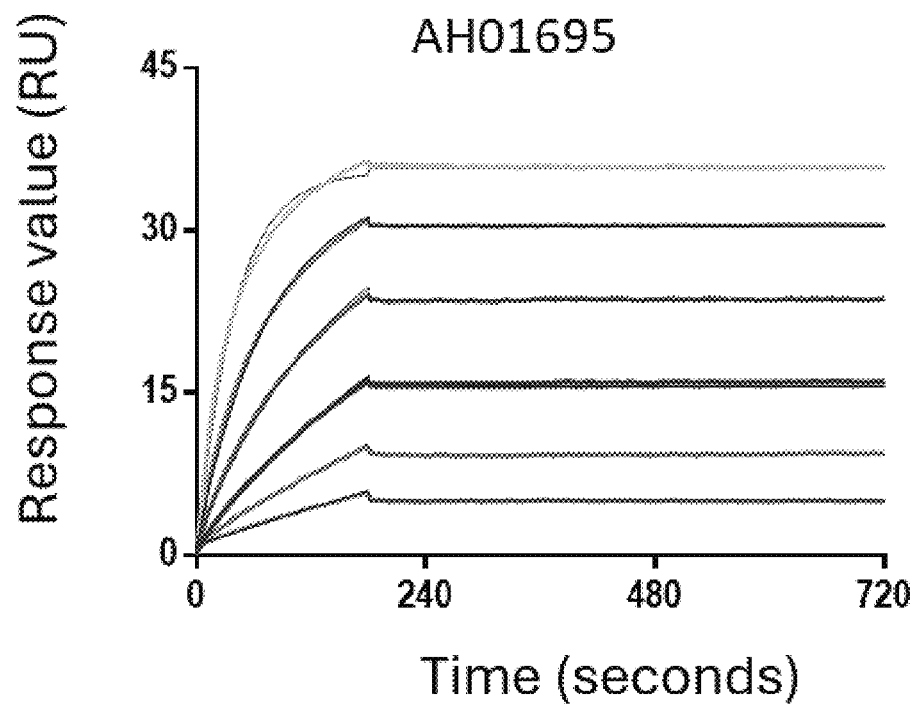
Figure 1G:
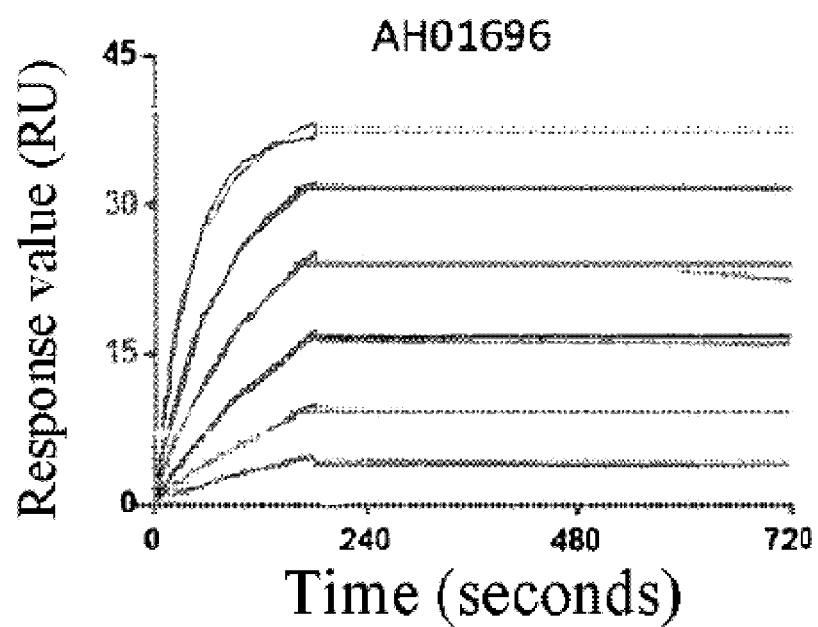
Figure 1H:
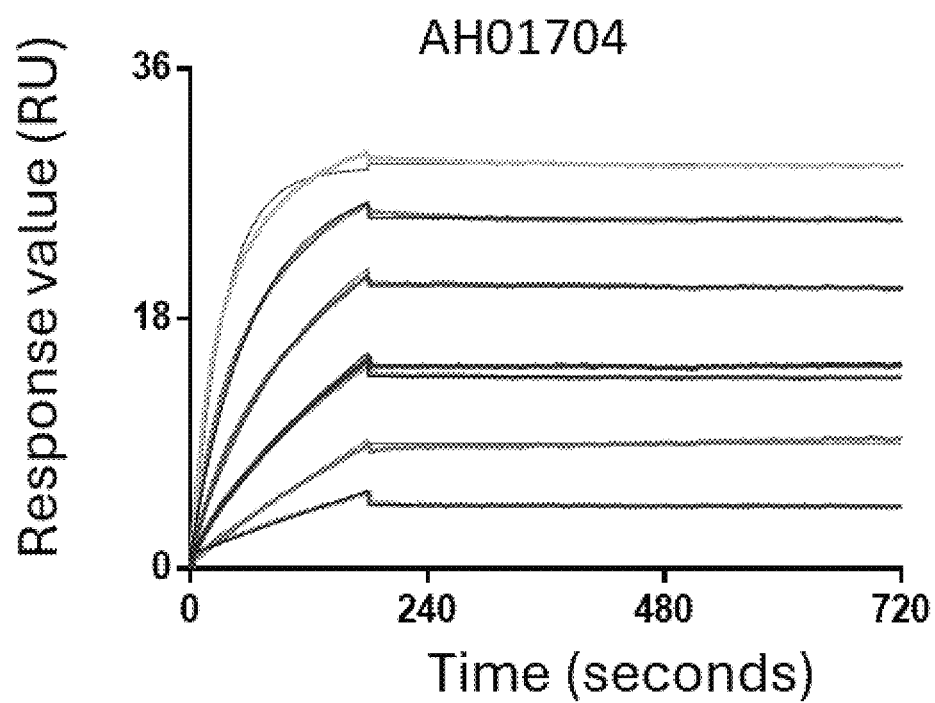

As shown in FIGS. 1A-1H and Table 4, the affinities of monoclonal antibodies specific to human CTLA4-Fc (AH01672, AH01674, AH01679, AH01686, AH01695, AH01696, AH01704) against human CTLA4-Fc were measured by Biacore and all reached sub-nM Level to pM level. These results indicated that the antibodies screened in the present invention had very high affinity.

TABLE 4

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| Chimeric antibody | CTLA4/His | 4.34E+05 | 1.00E−05 | 2.30E−11 | 40.6 | 5.32E−02 |
| AH01672 | | 6.90E+05 | 1.00E−05 | 1.45E−11 | 38.2 | 5.48E−02 |
| AH01674 | | 7.05E+05 | 1.00E−05 | 1.42E−11 | 38.2 | 5.28E−02 |
| AH01679 | | 7.48E+05 | 1.00E−05 | 1.34E−11 | 36.5 | 4.83E−02 |
| AH01686 | | 8.20E+05 | 3.18E−05 | 3.88E−11 | 27 | 9.10E−02 |
| AH01695 | | 6.55E+05 | 1.00E−05 | 1.53E−11 | 36.2 | 4.96E−02 |
| AH01696 | | 6.46E+05 | 2.77E−05 | 4.29E−11 | 38.3 | 1.04E−01 |
| AH01704 | | 7.80E+05 | 1.12E−05 | 1.44E−11 | 29.3 | 5.27E−02 |

Example 4: Functional Verification of a Humanized Anti-Human CTLA4 Monoclonal Antibody The functional detection and analysis of an anti-human CTLA-4 antibody were carried out by using an anti-CTLA-4 blocking assay kit developed by Promega. The kit contained two cell lines, including CD80/CD86 aAPC/Raji stimulating cells and functional cells expressing CTLA-4. Without the addition of an anti-CTLA-4 antibody, Raji cells bound to CTLA-4 of functional cells to inhibit immune signal transmission without activating NFκB to bind to a downstream promoter sequence to achieve the expression of a reporter gene luc2. When an anti-human CTLA-4 antibody was added, the CTLA-4 protein was blocked, the immune response stimulated by Raji cells was reactivated, luciferase in the functional cells was expressed and reacted with a substrate, and fluorescent signals generated could be detected and collected.

In the experiment, Raji cells expressing CD80/CD86 and functional cells expressing CTLA-4 were cultured and counted. Raji cells were plated into a 96-well plate at 50,000 cells/well. Sample antibodies and positive and negative control antibodies were added into Raji cells according to a gradient, and then functional cells were added at 50,000 cells/well. Mixed incubation was carried out in a 5% $CO_2$ environment at 37° C. for 6 hours. A fluorescent reaction substrate was added for a reaction in the dark at room temperature for 10 minutes, and then the fluorescence intensity was detected. If an antibody had a CTLA-4 blocking effect, the fluorescence intensity showed an inverse curve with the increased antibody concentration.

Figure 2:
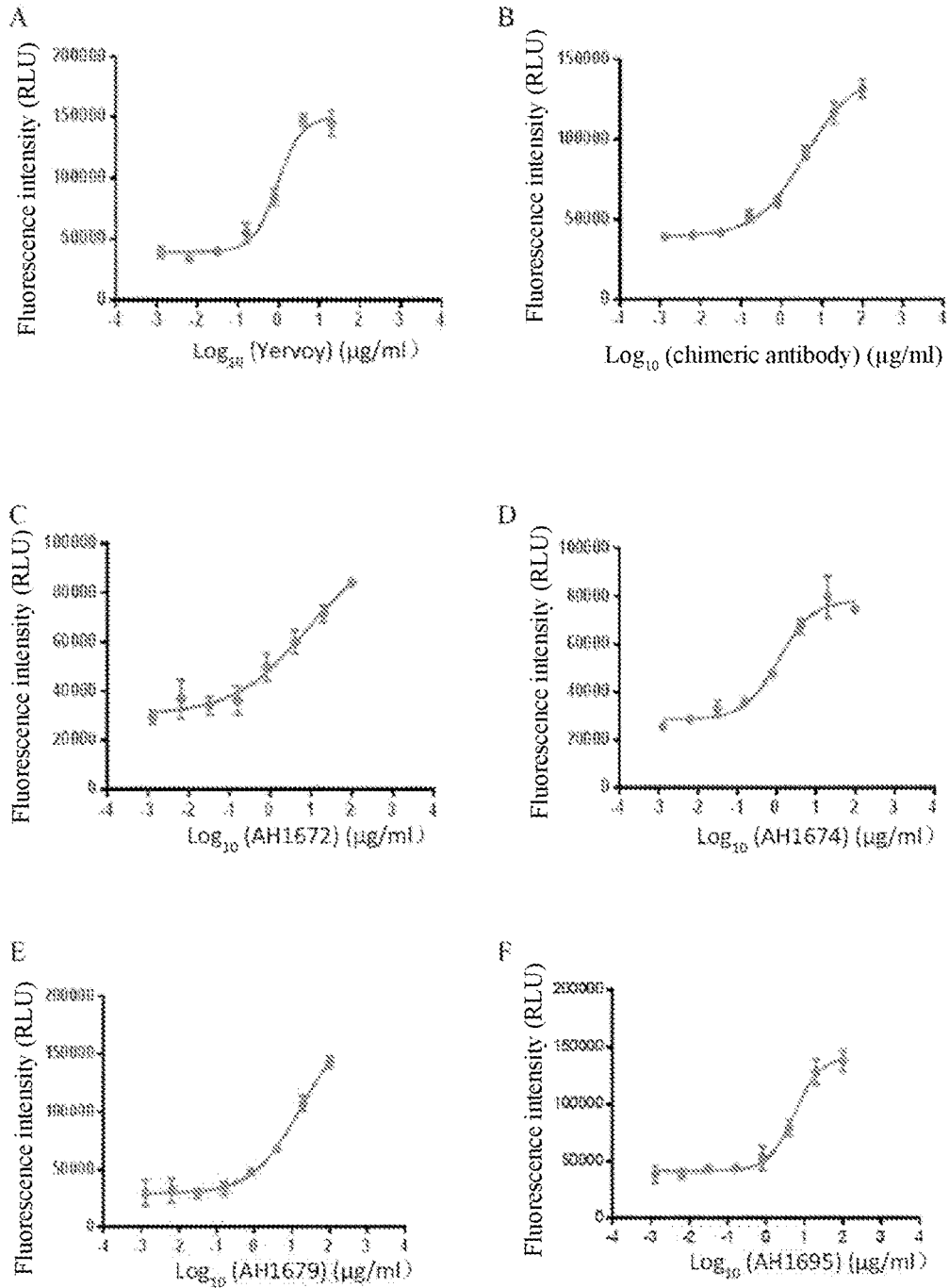
FIGS. 2A-2F show that purified monoclonal antibodies can relieve the negative immune regulation of CTLA4.

Experimental results showed that humanized anti-human CTLA4 monoclonal antibodies (AH01672, AH01674, AH01679, AH01695) could specifically relieve the negative immune regulation of CTLA4 and activate T cells to secrete cytokines. The corresponding EC50 was 7.310 μg/ml, 1.115 μg/ml, 17.10 μg/ml and 5.464 μg/ml (FIGS. 2A-2F and Table 5) respectively. Two humanized antibodies, AH01674 (1.115 μg/ml) and AH01695 (5.464 μg/ml), which had a lower EC50, were selected to advance the research of druggability and thermal stability.

TABLE 5

| Antibody name | Yervoy | Chimeric antibody | AH1672 | AH1674 | AH1679 | AH1695 |
|---|---|---|---|---|---|---|
| EC50 (μg/ml) | 0.9334 | 3.960 | 7.310 | 1.115 | 17.10 | 5.464 |

Example 5: Druggability Evaluation of a Humanized Anti-Human CTLA4 Monoclonal Antibody The three antibodies AH01674, AH01695 and a chimeric antibody were expressed in a 200 ml system to obtain 5 mg or higher purified antibody samples in which endotoxin was controlled at the level of 3 EU/mg for subsequent experiments.

1. Thermal Stability Detection
Thermal stability detection experiment setup
   A. The antibody sample concentration was higher than 5 mg/ml for a durability test.

The antibody samples were treated separately at 40° C. and then centrifuged to remove the precipitate, and the amount of remaining antibodies was evaluated by ELISA. (Treatment was carried out at 40° C. for 7 days, separate detection was carried out for 14 days, and an untreated sample stored at −80° C. was used as a control for each detection at the same time.)
   B. The concentration of each antibody sample was higher than 5 mg/ml, the samples were treated at five gradients of room temperature, 30° C., 40° C., 50° C. and 60° C. for 20 minutes separately and then centrifuged to remove the precipitate, and then ELISA was used to evaluate the amount of remaining antibodies. An untreated sample stored at −80° C. was used as a control for each detection at the same time.

A/B treated samples were sent to SEC-HPLC for detection at the same time.

Figure 3A:
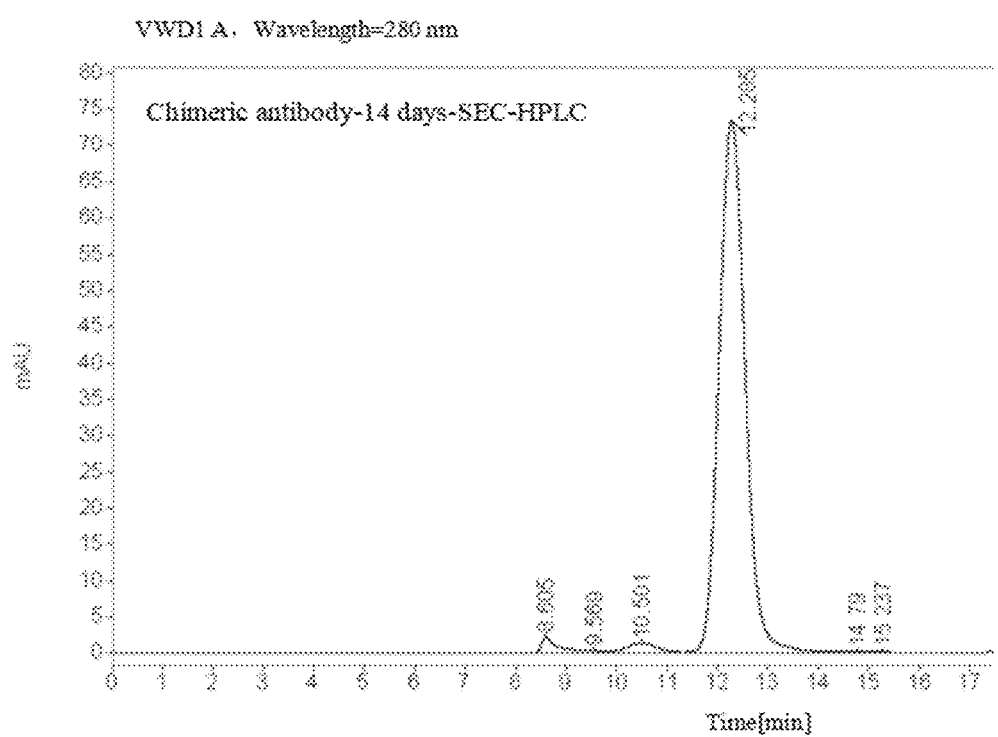
FIGS. 3A-3C show thermal stability analysis of purified monoclonal antibodies, specifically SEC-HPLC analysis of thermal stability of humanized anti-human CTLA4 monoclonal antibodies (treated at 40° C. for 2 weeks): chimeric antibody-14 days-SEC-HPLC (FIG. 3A), AH01674-14 days-SEC-HPLC (FIG. 3B) and AH01695-14 days-SEC-HPLC (FIG. 3C)
Figure 3B:
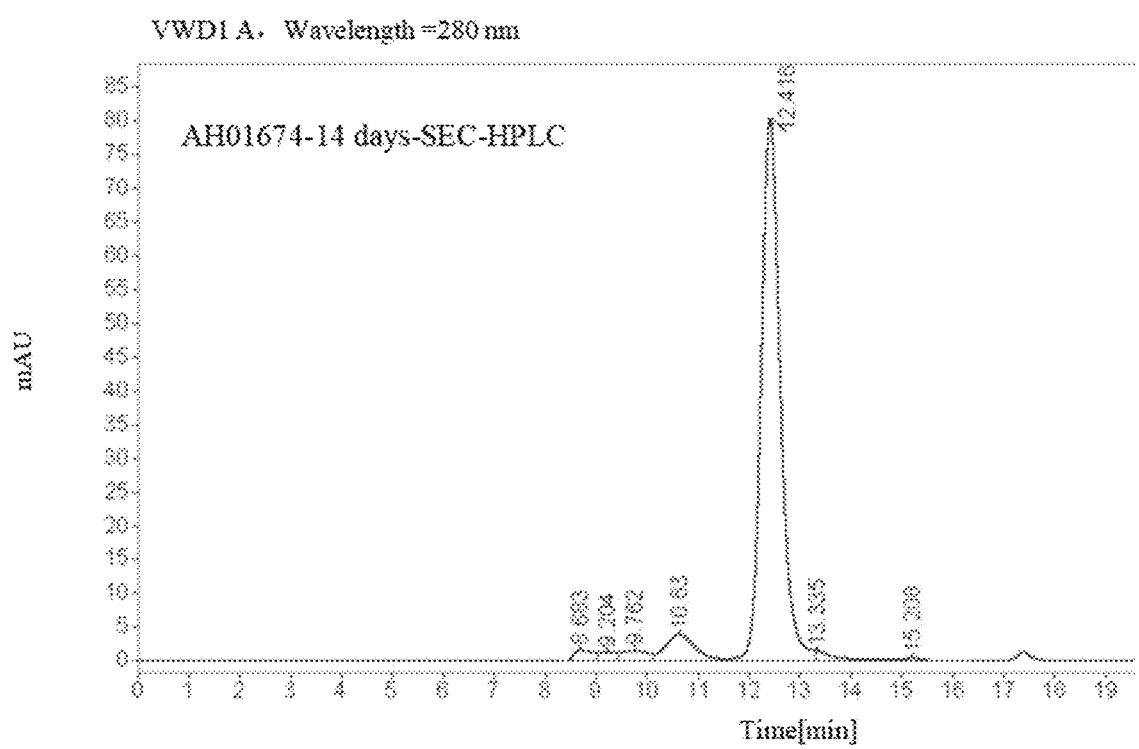
Figure 3C:
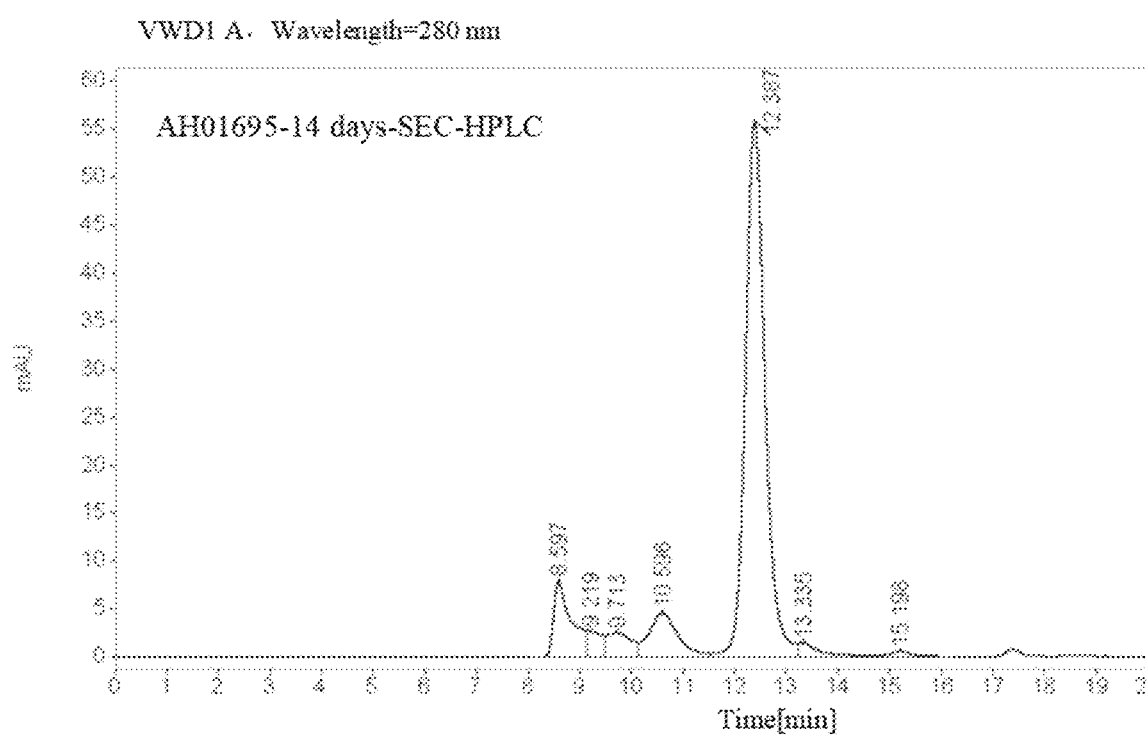
Figure 4:
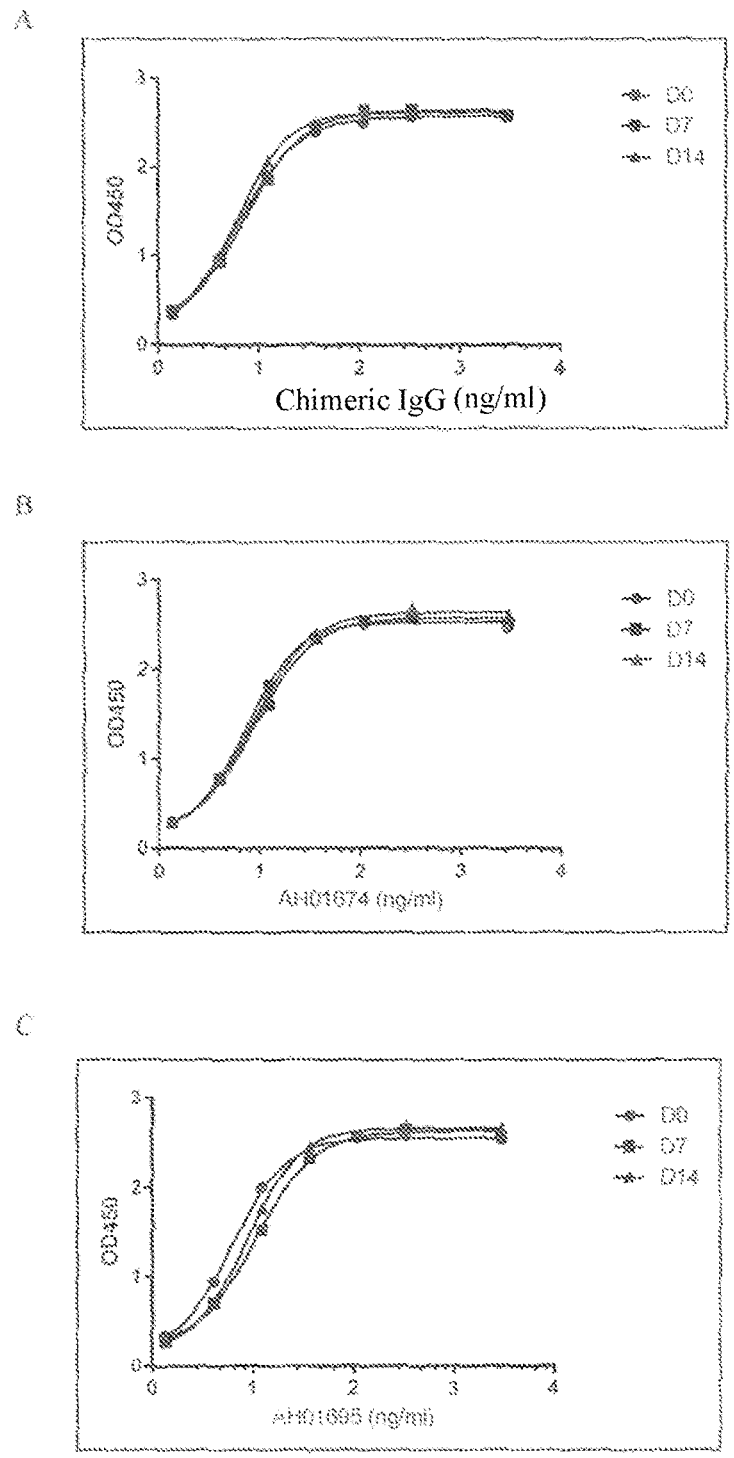
FIGS. 4A-4C show thermal stability analysis of purified monoclonal antibodies, specifically ELISA analysis of thermal stability of humanized anti-human CTLA4 monoclonal antibodies (treated at 40° C. for 2 weeks): a chimeric antibody (also referred to as "Chimeric IgG" herein and in the accompanying drawings, and the two can be used interchangeably) (FIG. 4A), AH01674 (FIG. 4B) and AH01695 (FIG. 4C)
Figure 5:
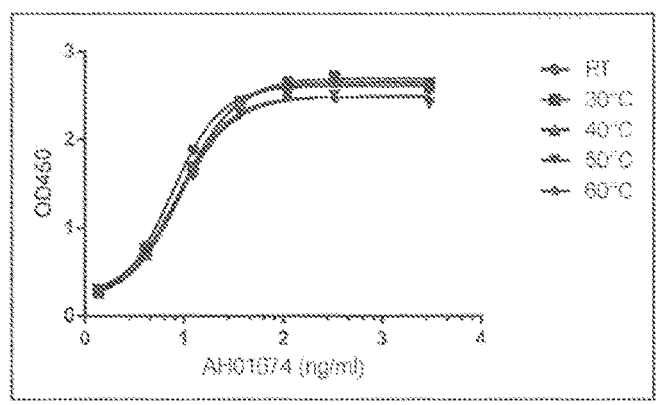
FIGS. 5A-5B show thermal stability analysis of purified monoclonal antibodies, specifically ELISA analysis of thermal stability of humanized anti-human CTLA4 monoclonal antibodies (temperature gradient): AH01674 (FIG. 5A) and AH01695 (FIG. 5B)
Figure 5:
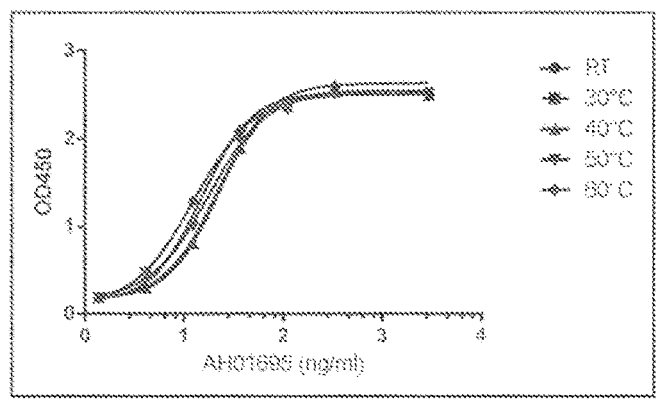

The results were shown in FIGS. 3A-3C, 4A-C and 5A-5B. The three heat-treated antibody samples AH01674, AH01695 and a chimeric antibody did not show a large amount of aggregation, and at the same time showed a stable antibody-antigen binding ability.

2. A druggability Experiment

The CDR region sequence analysis of an anti-human CTLA4 monoclonal antibody (Table 1) showed that the VH region was predicted to have hot spots of oxidation modification at W33 and M63 sites. The humanized anti-human CTLA4 monoclonal antibody was separately subjected to
   A. an oxidation pressure test: antibody molecules were transferred into a 20 mM ammonium acetate solution (pH 5.0), and AAPH (2,2'-azobis(2-amidinopropane)) (50:1) was added for treatment in the dark at 40° C. for 24 hours.
   B. a deamidation pressure test: antibody molecules were placed in a PBS solution (pH 9) at 40° C. for 48 hours to judge the effect of oxidation modification/deamidation modification on the antigen recognition ability of antibody molecules. The proportion of chemical changes in corresponding amino acid molecules of treated antibody samples was determined by mass spectrometric detection, the change of affinity was determined by Biocore, and the change of polymerization of the antibody molecules was determined by SEC-HPLC.

Figure 6A:
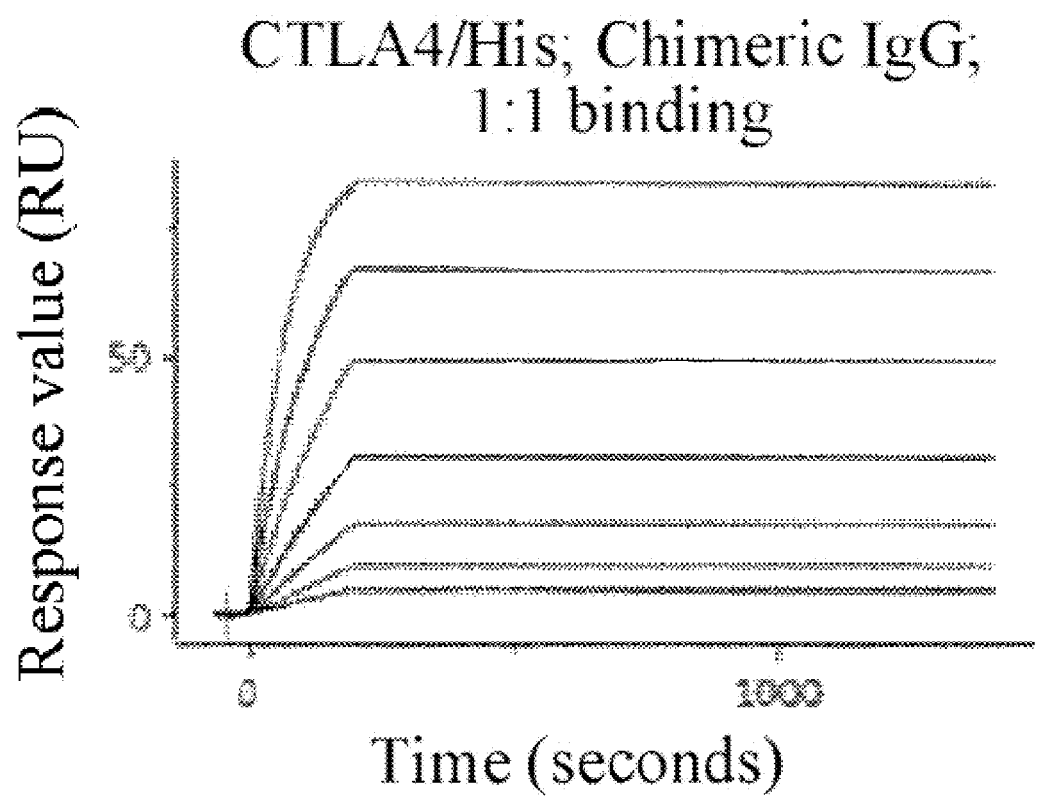
FIGS. 6A-6F show druggability detection and analysis of purified monoclonal antibodies, specifically the affinity detection of humanized anti-human CTLA4 monoclonal antibodies after an oxidation pressure test: a chimeric antibody (FIG. 6A), chimeric antibody-AAPH (FIG. 6B), AH01674 (FIG. 6C), AH01674-AAPH (FIG. 6D), AH01695 (FIG. 6E) and AH01695-AAPH (FIG. 6F)
Figure 6B:
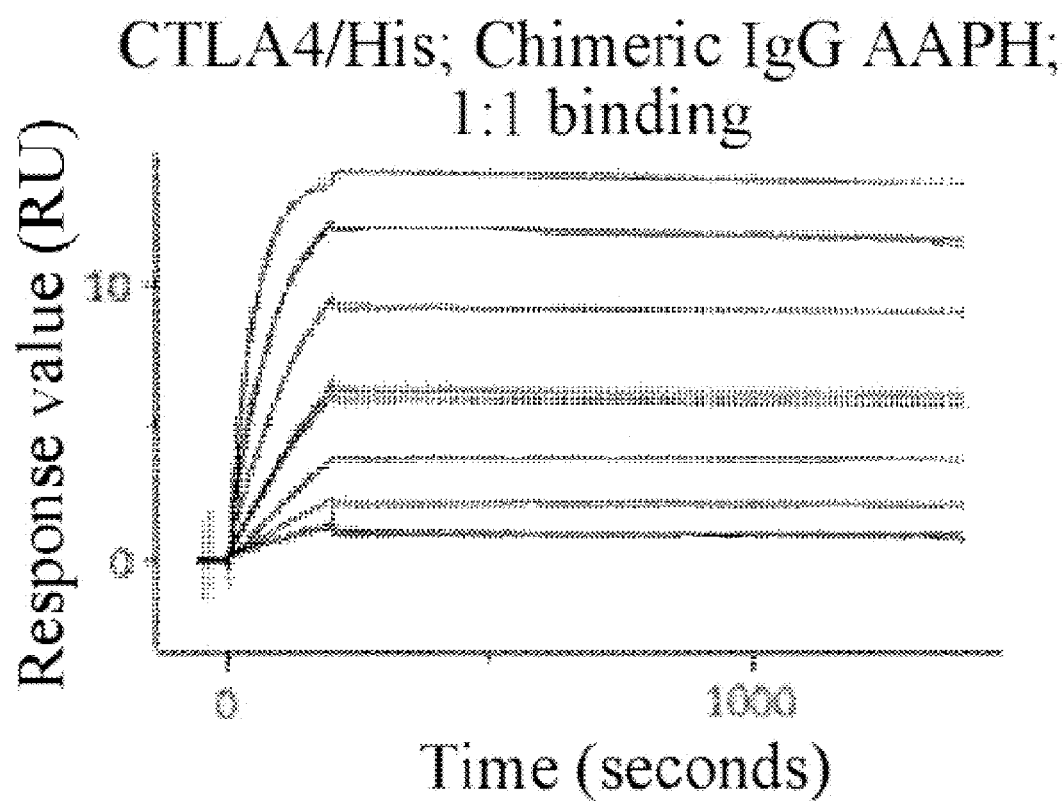
Figure 6C:
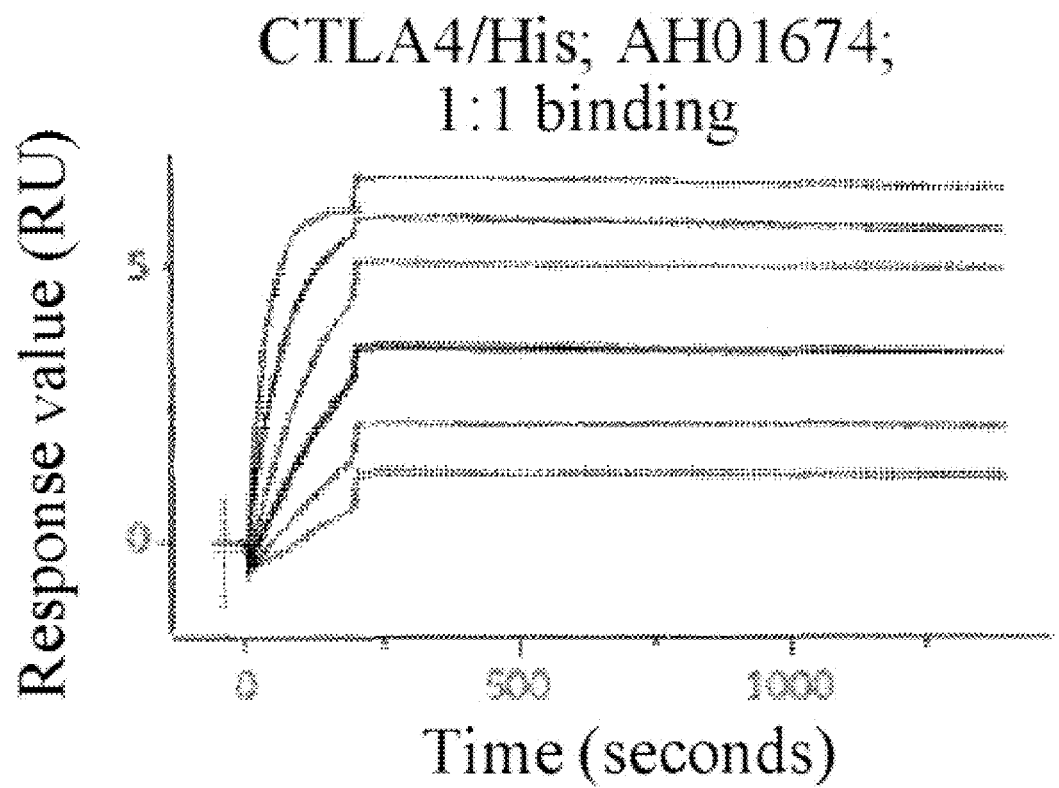
Figure 6D:
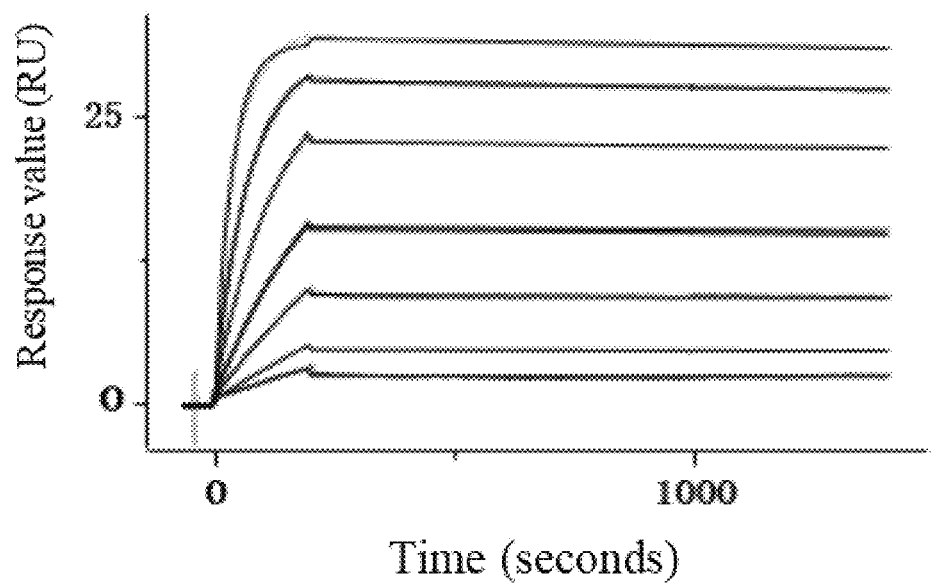
Figure 6E:
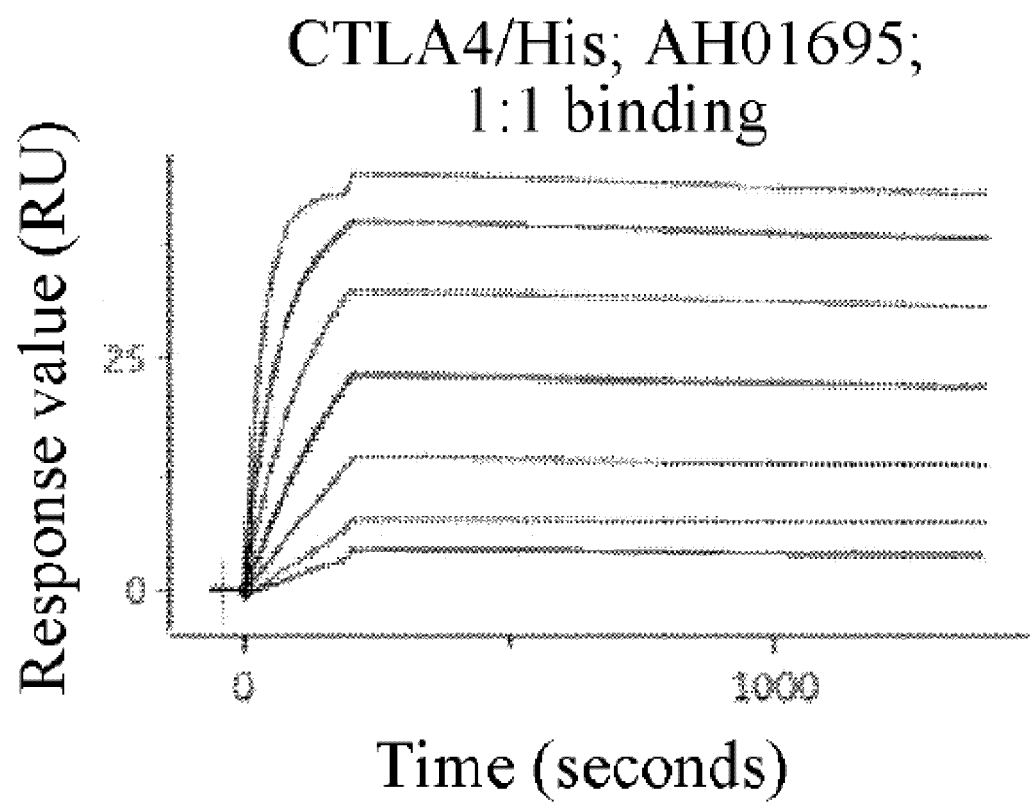
Figure 6F:
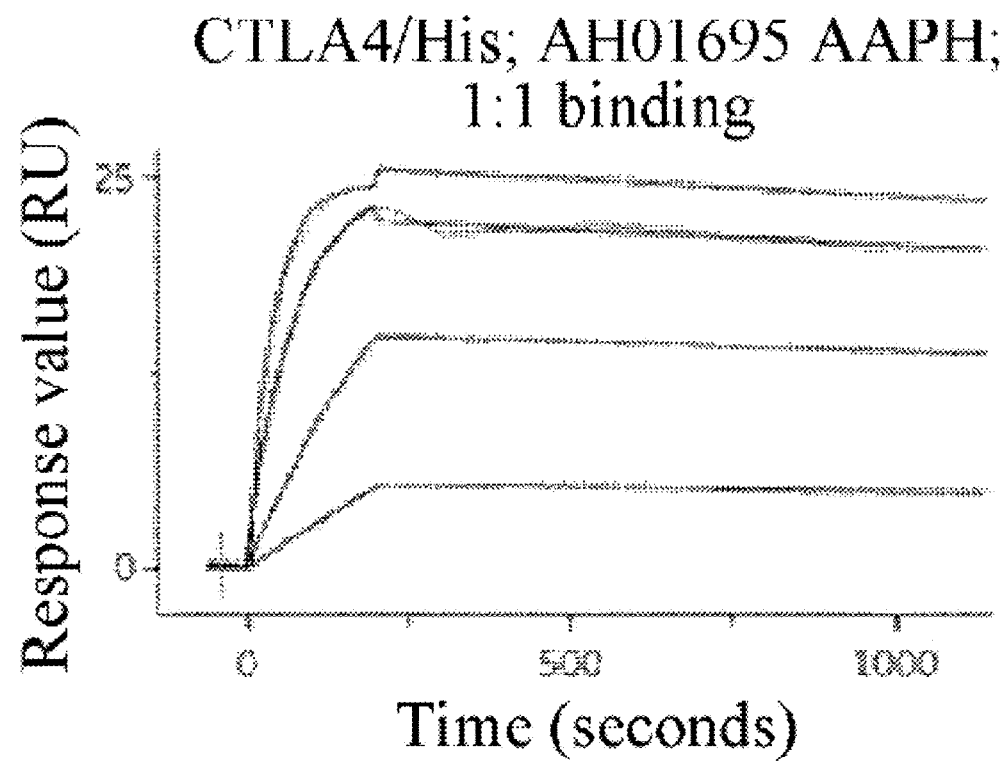
Figure 7A:
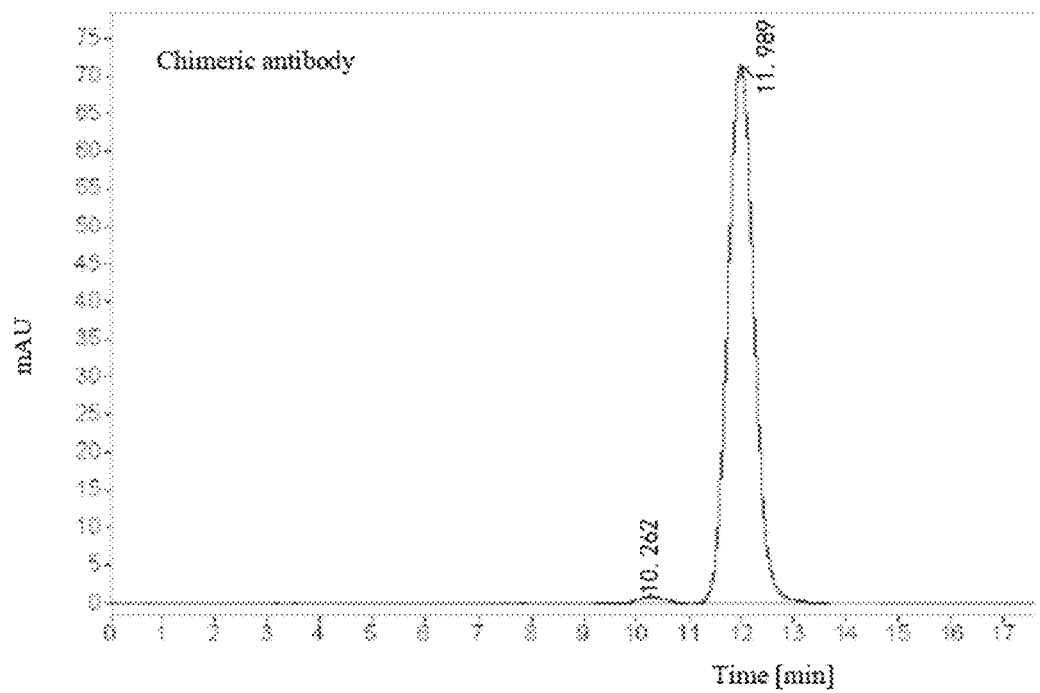
FIGS. 7A-7F show druggability detection and analysis of purified monoclonal antibodies, specifically the SEC detection of humanized anti-human CTLA4 monoclonal antibodies after an oxidation pressure test: a chimeric antibody (FIG. 7A), chimeric antibody-AAPH (FIG. 7B), AH01674
Figure 7B:
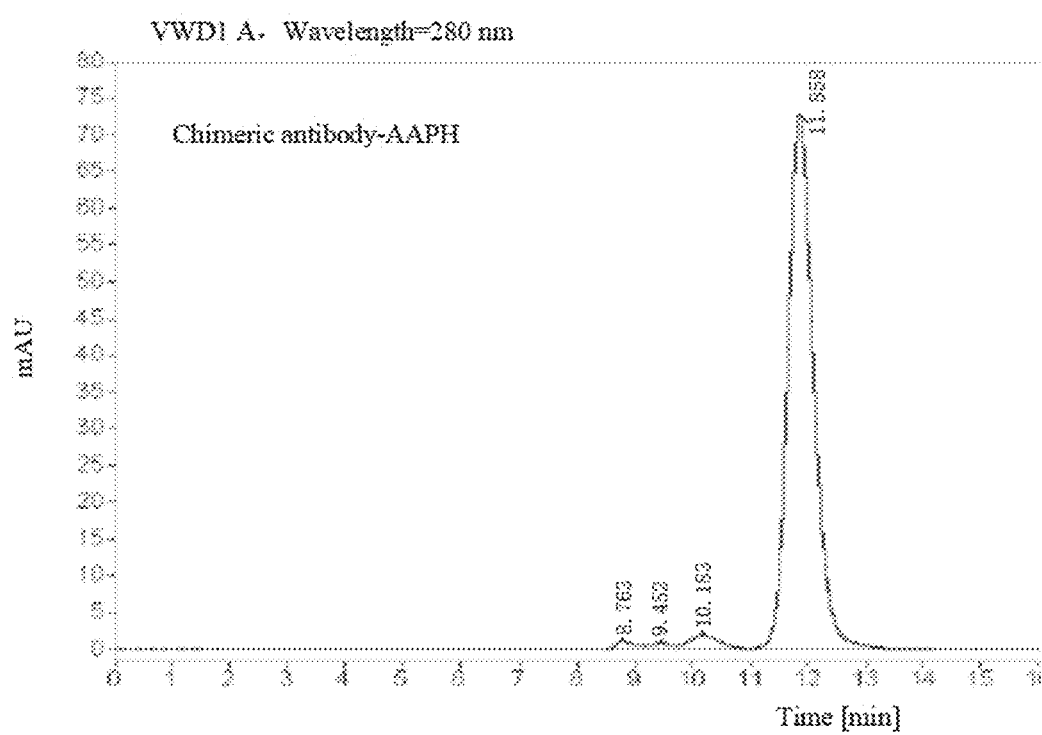
Figure 7C:
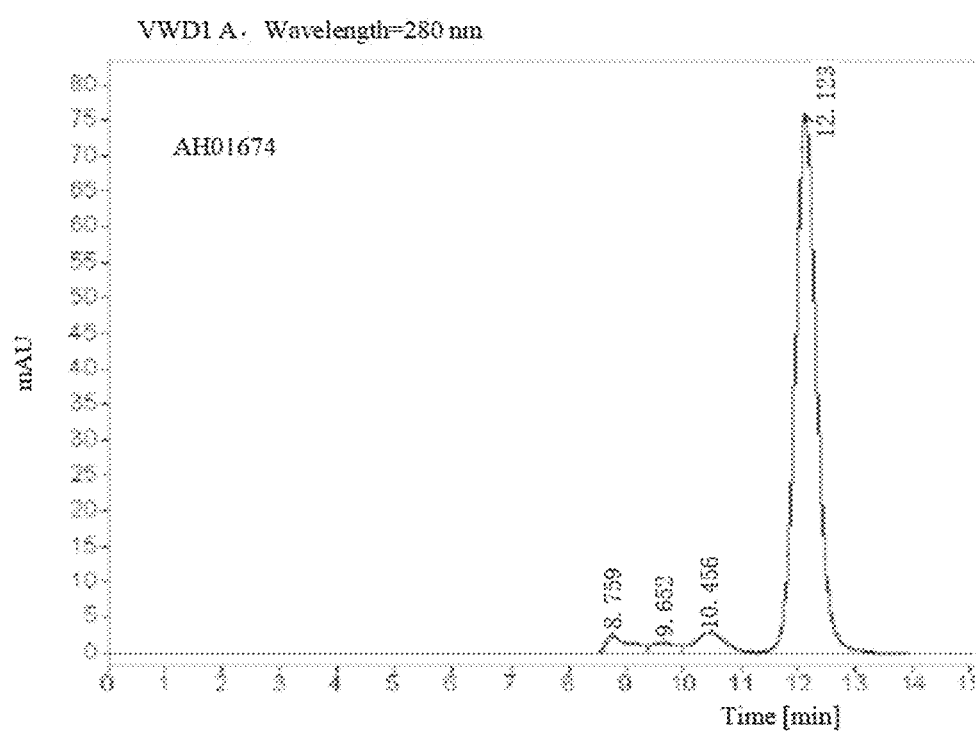
Figure 7D:
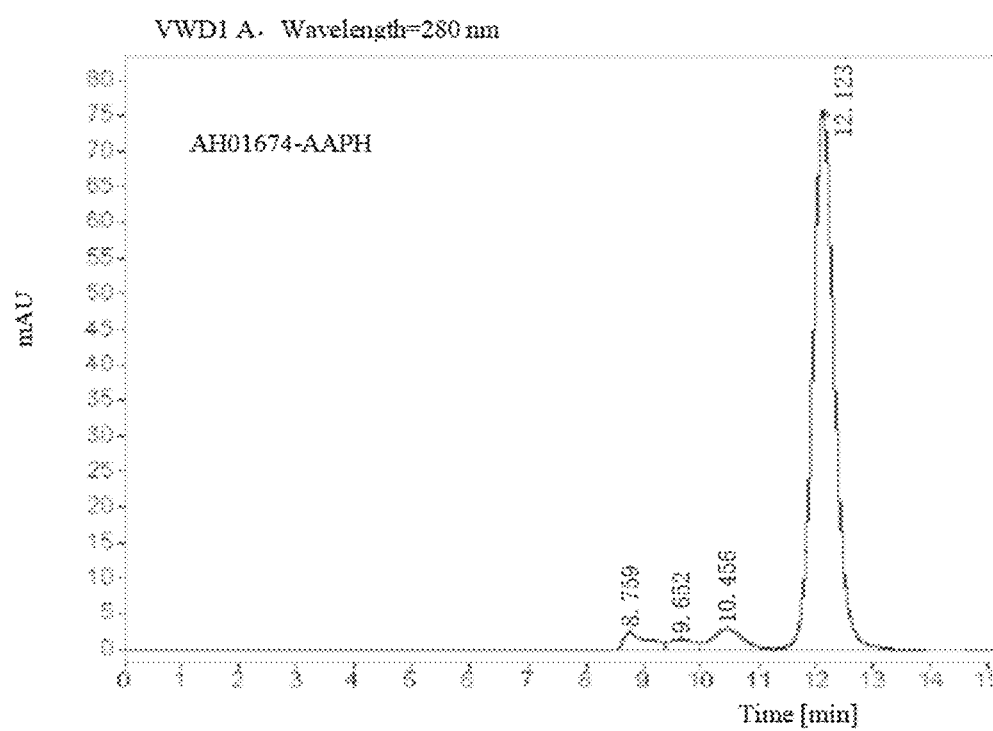
Figure 7E:
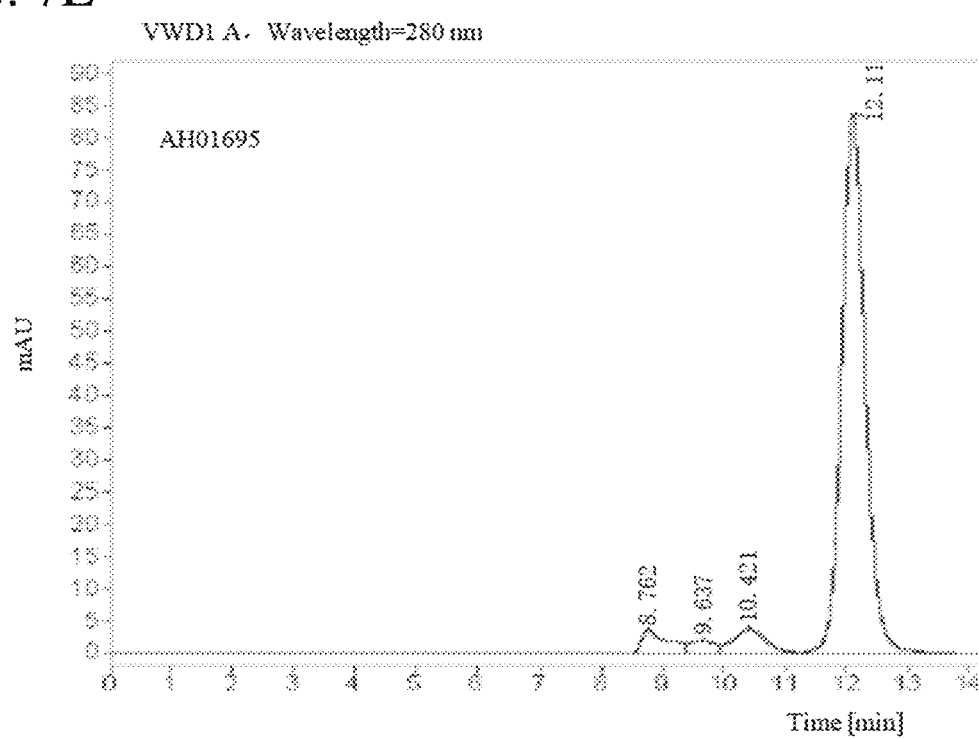
Figure 7F:
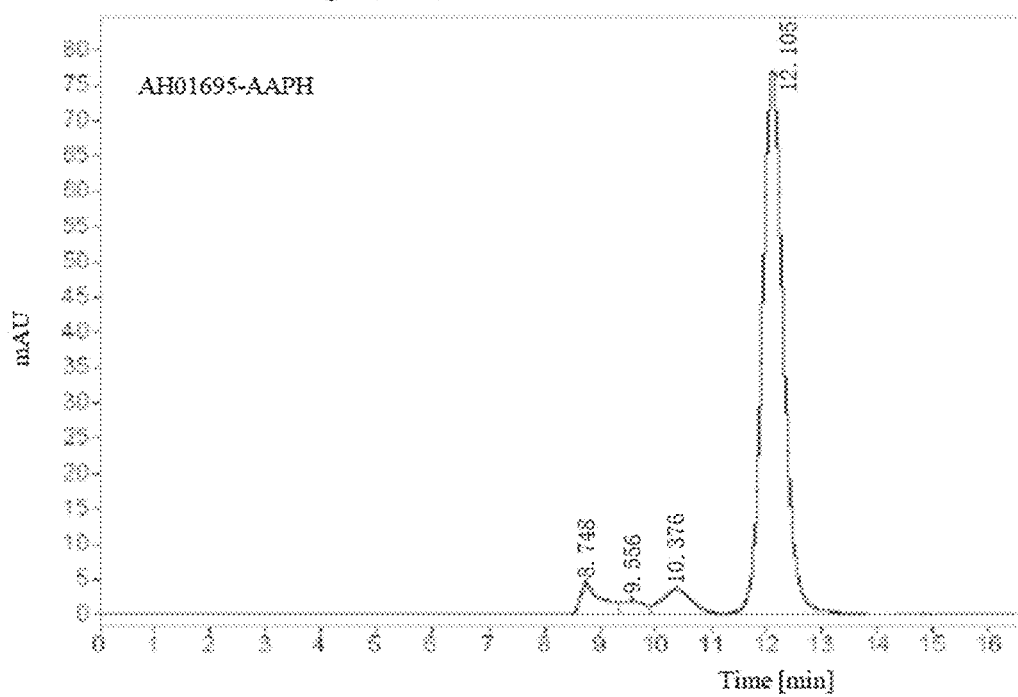

The results showed (Tables 6-8 and FIGS. 6A-F and 7A-7F) that the mass spectrometric detection coverage rate reached about 95%, and reliable results were obtained. In an antibody AH01674 control sample, 9.54% oxidation of M@63 was detected, and in an AAPH-24 treated sample, 75.62% oxidation of M@63 was detected. In an antibody AH01695 control sample, 8.91% oxidation of M@63 was detected, oxidation of M@250 was not detected, in an AAPH-24 treated sample, 70.90% oxidation of M@63 was detected, and 26.14% oxidation of M@250 was detected. M250 was located in the constant region of the antibody molecules. Therefore, there was the possibility of oxidation modification at the M63 site in the CDR sequences of AH01674 and AH01695.

The results of affinity verification and SEC verification showed that the oxidation pressure treatment of AH01674 and AH01695 antibody molecules did not affect the affinity of an antibody to an antigen and the homogeneity of antibody molecules.

At the same time, mass spectrometry analysis and detection of the deamidation pressure test showed that there was no deamidation modification in the CDR sequences of AH01674 and AH01695, which was consistent with the sequence analysis conclusion.

Table 6. Druggability Detection and Analysis: Mass Spectrometric Detection of a Humanized Anti-Human CTLA4 Monoclonal Antibody after an Oxidation Pressure Test

| Sample name | Sequence | Modification | Modification percentage | XIC area |
|---|---|---|---|---|
| Chimeric antibody control | YNEMFTGKATL (SEQ ID NO: 31) | | | 6.63E+05 |
| Chimeric antibody AAPH-24h | YNEMFTGKATL (SEQ ID NO: 31) | | | 3.98E+05 |
| | YNEMFTGKATL (SEQ ID NO: 31) | Oxidation@4(63) | 62.144 | 6.53E+05 |

-continued

| Sample name | Sequence | Modification | Modification percentage | XIC area |
|---|---|---|---|---|
| AH01674 control | YNEMFTGR (SEQ ID NO: 32) | | | 3.40E+06 |
| | YNEMFTGR (SEQ ID NO: 32) | Oxidation@4(63) | 9.538 | 3.59E+05 |
| AH01674 AAPH-24h | YNEMFTGR (SEQ ID NO: 32) | | | 1.19E+06 |
| | YNEMFTGR (SEQ ID NO: 32) | Oxidation@4(63) | 75.616 | 3.70E+06 |
| AH01695 control | YNEMFTGRVTL (SEQ ID NO: 33) | | | 1.62E+06 |
| | YNEMFTGRVTL (SEQ ID NO: 33) | Oxidation@4(63) | 8.913 | 1.58E+05 |
| | DTLMISR (SEQ ID NO: 34) | | | 1.35E+06 |
| AH01695 AAPH-24h | YNEMFTGRVTL (SEQ ID NO: 33) | | | 1.18E+06 |
| | YNEMFTGRVTL (SEQ ID NO: 33) | Oxidation@4(63) | 70.898 | 2.87E+06 |
| | DTLMISR (SEQ ID NO: 34) | | | 5.67E+05 |
| | DTLMISR (SEQ ID NO: 34) | Oxidation@4(250) | 26.143 | 2.01E+05 |

TABLE 7

Druggability detection and analysis: Affinity detection of a humanized anti-human CTLA4 monoclonal antibody after an oxidation pressure test

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| Chimeric antibody | CTLA4/His | 3.72E+05 | 8.16E-06 | 2.19E-11 | 88.4 | 3.63E-02 |
| Chimeric antibody AAPH | | 5.70E+05 | 2.78E-05 | 4.87E-11 | 14.2 | 9.25E-03 |
| AH01674 | | 7.53E+05 | 2.98E-05 | 3.95E-11 | 6.7 | 9.92E-03 |
| AH01674 AAPH | | 7.19E+05 | 2.19E-05 | 3.05E-11 | 31.9 | 2.26E-02 |
| AH01695 | | 7.67E+05 | 4.55E-05 | 5.94E-11 | 45.2 | 6.68E-02 |
| AH01695 AAPH | | 6.70E+05 | 8.75E-05 | 1.31E-10 | 25.8 | 1.03E-01 |

TABLE 8

Druggability detection and analysis: Mass spectrometric detection of a humanized anti-human CTLA4 monoclonal antibody after a deamidation pressure test

| Sample name | Peptide | Modification | Modification percentage |
|---|---|---|---|
| AH01674-control | T41-43 | Deamidation@2(136) | 3.245 |
| AH01674-control | T41-43 | | |
| AH01674-ph9-48h | T42-43 | Deamidation@2(137) | 2.84 |
| AH01674-ph9-48h | T42-43 | | |
| AH01674-control | T42-43 | Deamidation@2(137) | 10.597 |
| AH01674-control | T42-43 | | |
| AH01674-ph9-48h | T42-43 | Deamidation@2(137) | 11.833 |
| AH01674-ph9-48h | T42-43 | | |
| AH01674-control | T40 | Deamidation@1(157) | 3.83 |
| AH01674-control | T40 | | |
| AH01674-control | T40-41 | Deamidation@1(157) | 4.994 |
| AH01674-control | T40-41 | | |
| AH01674-ph9-48h | T40-41 | Deamidation@1(157) | 5.28 |
| AH01674-ph9-48h | T40-41 | | |
| AH01674-control | T63-65 | Deamidation@11(284) | 4.319 |
| AH01674-control | T63-65 | | |
| AH01674-ph9-48h | T63-65 | Deamidation@11(284) | 3.311 |
| AH01674-ph9-48h | T63-65 | | |
| AH01674-control | T89 | Deamidation@1(359) | 2.695 |
| AH01674-control | T89 | | |
| AH01674-ph9-48h | T89 | Deamidation@1(359) | 0.575 |
| AH01674-ph9-48h | T89 | | |
| AH01674-control | T108-109 | Ureamethylation@2(423), Deamidation@11(432) | 4.156 |
| AH01674-control | T108-109 | Ureamethylation@2(423), Deamidation@11(432) | |
| AH01674-control | T108-109 | Ureamethylation@2(423) | |
| AH01674-ph9-48h | T108-109 | Ureamethylation@2(423), Deamidation@11(432) | 4.176 |
| AH01674-ph9-48h | T108-109 | Ureamethylation@2(423), Deamidation@11(432) | |
| AH01674-ph9-48h | T108-109 | Ureamethylation@2(423) | |
| AH01674-control | T71-74 | Deamidation@9(313) | 2.1 |
| AH01674-control | T71-74 | | |
| AH01674-control | T71-75 | Deamidation@9(313) | 11.767 |
| AH01674-control | T71-75 | | |

TABLE 8-continued

Druggability detection and analysis: Mass spectrometric detection of a humanized anti-human CTLA4 monoclonal antibody after a deamidation pressure test

| Sample name | Peptide | Modification | Modification percentage |
|---|---|---|---|
| AH01674-ph9-48h | T71-74 | Deamidation@9(313) | 2.678 |
| AH01674-ph9-48h | T71-74 | | |
| AH01674-ph9-48h | T71-75 | Deamidation@9(313) | 9.999 |
| AH01674-ph9-48h | T71-75 | | |
| AH01674-control | T92-96 | | |
| AH01674-ph9-48h | T92-96 | Deamidation@19(387) | 14.689 |
| AH01674-ph9-48h | T92-96 | | |
| AH01695-control | T41-43 | Deamidation@2(136) | 2.934 |
| AH01695-control | T41-43 | | |
| AH01695-ph9-48h | T41-43 | Deamidation@2(136) | 3.73 |
| AH01695-ph9-48h | T41-43 | | |
| AH01695-control | T42-43 | Deamidation@2(137) | 12.049 |
| AH01695-control | T42-43 | | |
| AH01695-ph9-48h | T42-43 | Deamidation@2(137) | 11.621 |
| AH01695-ph9-48h | T42-43 | | |
| AH01695-control | T42-43 | Deamidation@1(157) | 5.666 |
| AH01695-control | T42-43 | | |
| AH01695-ph9-48h | T42-43 | Deamidation@1(157) | 5.315 |
| AH01695-ph9-48h | T42-43 | | |
| AH01695-control | T65-67 | Deamidation@11(284) | 2.378 |
| AH01695-control | T65-67 | | |
| AH01695-ph9-48h | T65-67 | Deamidation@11(284) | 2.323 |
| AH01695-ph9-48h | T65-67 | | |
| AH01695-ph9-48h | T91 | Deamidation@1(359) | 0.501 |
| AH01695-ph9-48h | T91 | | |
| AH01695-control | T110-111 | Ureamethylation@2(423), Deamidation@11(432) | 3.608 |
| AH01695-control | T110-111 | Ureamethylation@2(423), Deamidation@11(432) | 3.608 |
| AH01695-control | T110-111 | Ureamethylation@2(423) | |
| AH01695-ph9-48h | T110-111 | Ureamethylation@2(423), Deamidation@11(432) | 3.776 |
| AH01695-ph9-48h | T110-111 | Ureamethylation@2(423), Deamidation@11(432) | 3.776 |
| AH01695-ph9-48h | T110-111 | Ureamethylation@2(423) | |
| AH01695-control | T73-76 | Deamidation@9(313) | 2.476 |
| AH01695-control | T73-76 | | |
| AH01695-ph9-48h | T73-76 | Deamidation@9(313) | 1.904 |
| AH01695-ph9-48h | T73-76 | | |
| AH01695-control | T92-96 | | |
| AH01695-ph9-48h | T92-96 | Deamidation@19(387) | 15.33 |
| AH01695-ph9-48h | T92-96 | | |
| Chimeric-0h | T38-39 | | |
| Chimeric-ph9-48h | T37-39 | Deamidation@2(137) | 9.531 |
| Chimeric-ph9-48h | T37-39 | | |
| Chimeric-ph9-48h | T38-39 | Deamidation@2(136) | 3.735 |
| Chimeric-ph9-48h | T38-39 | | |
| Chimeric-0h | T38-39 | Deamidation@1(136) | 10.057 |
| Chimeric-0h | T93 | | |
| Chimeric-0h | T93 | Deamidation@1(359) | 2.211 |
| Chimeric-ph9-48h | T93 | | |
| Chimeric-ph9-48h | T93 | Deamidation@1(359) | 2.672 |
| Chimeric-ph9-48h | T93 | Deamidation@1(359) | 2.672 |
| Chimeric-0h | T44 | | |
| Chimeric-0h | T44 | Deamidation@1(157) | 4.112 |
| Chimeric-0h | T44-45 | | |
| Chimeric-0h | T44-45 | Deamidation@1(157) | 5.232 |
| Chimeric-ph9-48h | T44 | | |
| Chimeric-ph9-48h | T44 | Deamidation@1(157) | 4.158 |
| Chimeric-ph9-48h | T44-45 | | |
| Chimeric-ph9-48h | T44-45 | Deamidation@1(157) | 5.457 |
| Chimeric-0h | T66-69 | | |
| Chimeric-0h | T66-69 | Deamidation@12(284) | 2.719 |
| Chimeric-ph9-48h | T66-69 | | |
| Chimeric-ph9-48h | T66-69 | Deamidation@12(284) | 1.989 |
| Chimeric-ph9-48h | T67-69 | | |
| Chimeric-ph9-48h | T67-69 | Deamidation@11(284) | 3.146 |
| Chimeric-0h | T112-113 | Ureamethylation@2(423) | |
| Chimeric-0h | T112-113 | Ureamethylation@2(423), Deamidation@11(432) | 3.936 |
| Chimeric-0h | T112-113 | Ureamethylation@2(423), Deamidation@11(432) | 3.936 |
| Chimeric-ph9-48h | T112-113 | Ureamethylation@2(423) | |
| Chimeric-ph9-48h | T112-113 | Ureamethylation@2(423), Deamidation@11(432) | 4.317 |
| Chimeric-ph9-48h | T112-113 | Ureamethylation@2(423), Deamidation@11(432) | 4.317 |
| Chimeric-0h | T75-78 | | |
| Chimeric-0h | T75-78 | Deamidation@9(313) | 2.021 |
| Chimeric-0h | T75-79 | | |
| Chimeric-0h | T75-79 | Deamidation@9(313) | 9.676 |
| Chimeric-ph9-48h | T75-79 | | |
| Chimeric-ph9-48h | T75-79 | Deamidation@9(313) | 8.446 |
| Chimeric-0h | T96-100 | | |
| Chimeric-ph9-48h | T96-100 | Deamidation@19(387) | 12.52 |
| Chimeric-ph9-48h | T96-100 | | |

The invention claimed is:

1. A humanized anti-human cytotoxic T-lymphocyte associated protein 4 (CTLA4) monoclonal antibody or a functional fragment thereof, comprising a heavy chain variable region and a light chain variable region, wherein the heavy chain variable region comprises the amino acid sequences of the following heavy chain complementarity determining regions (HCDRs) HCDR1, HCDR2 and HCDR3 sequences, and the light chain variable region comprises the amino acid sequences of the following light chain complementarity determining regions (LCDRs) LCDR1, LCDR2 and LCDR3 sequences; wherein
the amino acid sequence of HCDR1 is

SYWIN; (SEQ ID NO: 25)

the amino acid sequence of HCDR2 is

RIAPGSGTTYYNEMFTG; (SEQ ID NO: 26)

the amino acid sequence of HCDR3 is

GDYFDY; (SEQ ID NO: 27)

the amino acid sequence of LCDR1 is

SASKSVSYIH; (SEQ ID NO: 28)

the amino acid sequence of LCDR2 is

DTSTLAS; (SEQ ID NO: 29)

and
the amino acid sequence of LCDR3 is

QQRTTYPLT. (SEQ ID NO: 30)

2. The humanized anti-human CTLA4 monoclonal antibody or a functional fragment thereof according to claim 1, wherein the amino acid sequence of the heavy chain variable region is SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16.

3. The humanized anti-human CTLA4 monoclonal antibody or a functional fragment thereof according to claim 1, wherein the amino acid sequence of the light chain variable region is SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24.

4. The humanized anti-human CTLA4 monoclonal antibody or a functional fragment thereof according to claim 1, wherein
the heavy chain variable region is SEQ ID NO: 9 and the light chain variable region is SEQ ID NO: 17;
the heavy chain variable region is SEQ ID NO: 10 and the light chain variable region is SEQ ID NO: 18;
the heavy chain variable region is SEQ ID NO: 11 and the light chain variable region is SEQ ID NO: 19;
the heavy chain variable region is SEQ ID NO: 12 and the light chain variable region is SEQ ID NO: 20;
the heavy chain variable region is SEQ ID NO: 13 and the light chain variable region is SEQ ID NO: 21;
the heavy chain variable region is SEQ ID NO: 14 and the light chain variable region is SEQ ID NO: 22;
the heavy chain variable region is SEQ ID NO: 15 and the light chain variable region is SEQ ID NO: 23; or
the heavy chain variable region is SEQ ID NO: 16 and the light chain variable region is SEQ ID NO: 24.

5. The humanized anti-human CTLA4 monoclonal antibody or a functional fragment thereof according to claim 2, wherein a dissociation constant KD between the humanized anti-human CTLA4 monoclonal antibody or a functional fragment thereof and CLTA4 is lower than 0.02 nM.

6. An isolated polynucleotide encoding the humanized anti-human CTLA4 monoclonal antibody or a functional fragment thereof according to claim 1.

7. An isolated polynucleotide, comprising a sequence encoding the heavy chain variable region of the humanized anti-human CTLA4 monoclonal antibody or a functional fragment thereof according to claim 1, and/or a sequence encoding the light chain variable region of the humanized anti-human CTLA4 monoclonal antibody or a functional fragment thereof according to claim 1.

8. An expression vector comprising the polynucleotide according to claim 6.

9. A host cell comprising the expression vector according to claim 8.

10. A method of treating a tumors in a subject in need thereof, comprising administering to the subject an effective amount of the humanized anti-human CTLA4 monoclonal antibody or a functional fragment thereof according to claim 1.

11. The method according to claim 10, wherein the tumor is multiple myeloma, non-small cell lung cancer, colorectal cancer, renal cell carcinoma, prostate cancer, breast cancer, or ovarian cancer.

12. An anti-tumor pharmaceutical composition comprising an effective amount of the humanized anti-human CTLA4 monoclonal antibody or a functional fragment thereof according to claim 1 and a pharmaceutically acceptable carrier.

13. A method for preparing a humanized anti-human CTLA4 monoclonal antibody or a functional fragment thereof, comprising transfecting competent cells with the expression vector according to claim 8 and culturing the competent cells.

14. An expression vector comprising the polynucleotide according to claim 7.

15. A method of treating a tumors in a subject in need thereof,
comprising administering to the subject an effective amount of the humanized anti-human CTLA4 monoclonal antibody or a functional fragment thereof according to claim 4.

16. The method according to claim 15, wherein the tumor is multiple myeloma, non-small cell lung cancer, colorectal cancer, renal cell carcinoma, prostate cancer, breast cancer, or ovarian cancer.

17. A humanized anti-human CTLA4 monoclonal antibody or a functional fragment thereof according to claim 4, wherein a dissociation constant KD between the humanized anti-human CTLA4 monoclonal antibody or a functional fragment thereof and CLTA4 is lower than 0.02 nM.

18. An isolated polynucleotide encoding the humanized anti-human CTLA4 monoclonal antibody or a functional fragment thereof according to claim 4.

19. An expression vector comprising the polynucleotide according to claim 18.

* * * * *

SEQUENCE LISTING

```
<160> NUMBER OF SEQ ID NOS: 34

<210> SEQ ID NO 1
<211> LENGTH: 115
<212> TYPE: PRT
<213> ORGANISM: Artificial Sequence
<220> FEATURE:
<223> OTHER INFORMATION: 42B11G12D3-VH

<400> SEQUENCE: 1

Gln Val His Leu Gln Gln Ser Gly Asp Val Leu Val Lys Pro Gly Ala
1               5                   10                  15

Ser Val Asn Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly Arg Ile Ala Pro Gly Ser Gly Thr Thr Tyr Tyr Asn Glu Met Phe
    50                  55                  60
```

```
Thr Gly Lys Ala Thr Leu Thr Val Val Thr Ser Ser Thr Ala Tyr
 65                  70                  75                  80

Ile Gln Leu Ser Ser Leu Ser Phe Glu Asp Ser Ala Val Tyr Phe Cys
                 85                  90                  95

Ala Arg Gly Asp Tyr Phe Asp Tyr Trp Asp Gln Gly Thr Thr Leu Thr
            100                 105                 110

Val Ser Ser
        115

<210> SEQ ID NO 2
<211> LENGTH: 106
<212> TYPE: PRT
<213> ORGANISM: Artificial Sequence
<220> FEATURE:
<223> OTHER INFORMATION: 42B11G12D3-VL

<400> SEQUENCE: 2

Gln Ile Val Leu Thr Gln Ser Pro Ala Ile Met Ser Ala Ser Pro Gly
 1               5                  10                  15

Gly Lys Val Thr Ile Thr Cys Ser Ala Ser Lys Ser Val Ser Tyr Ile
                20                  25                  30

His Trp Phe Gln Gln Lys Pro Gly Thr Ser Pro Lys Leu Leu Ile Tyr
             35                  40                  45

Asp Thr Ser Thr Leu Ala Ser Gly Val Pro Pro Arg Phe Ser Gly Ser
 50                  55                  60

Gly Ser Gly Pro Ser Tyr Ser Leu Thr Ile Ser Arg Met Glu Ala Glu
 65                  70                  75                  80

Asp Ala Ala Thr Tyr Tyr Cys Gln Gln Arg Thr Thr Tyr Pro Leu Thr
                 85                  90                  95

Phe Gly Gly Gly Thr Lys Leu Glu Val Arg
            100                 105

<210> SEQ ID NO 3
<211> LENGTH: 115
<212> TYPE: PRT
<213> ORGANISM: Artificial Sequence
<220> FEATURE:
<223> OTHER INFORMATION: 42B11G12D3-VH-GRAFTED

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
             35                  40                  45

Gly Arg Ile Ala Pro Gly Ser Gly Thr Thr Tyr Tyr Asn Glu Met Phe
 50                  55                  60

Thr Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ile Gly Asp Tyr Phe Asp Tyr Trp Gly Gln Gly Thr Met Val Thr
            100                 105                 110

Val Ser Ser
        115
```

```
<210> SEQ ID NO 4
<211> LENGTH: 106
<212> TYPE: PRT
<213> ORGANISM: Artificial Sequence
<220> FEATURE:
<223> OTHER INFORMATION: 42B11G12D3-VL-GRAFTED

<400> SEQUENCE: 4

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gln Gly Thr Lys Leu Glu Ile Lys
            100                 105

<210> SEQ ID NO 5
<211> LENGTH: 115
<212> TYPE: PRT
<213> ORGANISM: Artificial Sequence
<220> FEATURE:
<223> OTHER INFORMATION: 42B11G12D3-VH-CBM

<400> SEQUENCE: 5

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Ala Pro Gly Gln Gly Leu Glu Trp Ile
        35                  40                  45

Gly Arg Ile Ala Pro Gly Ser Gly Thr Thr Tyr Tyr Asn Glu Met Phe
    50                  55                  60

Thr Gly Arg Val Thr Leu Thr Arg Asp Thr Ser Thr Ser Thr Ala Tyr
65                  70                  75                  80

Ile Glu Leu Ser Ser Leu Arg Ser Glu Asp Thr Ala Val Tyr Phe Cys
                85                  90                  95

Ala Arg Gly Asp Tyr Phe Asp Tyr Trp Asp Gln Gly Thr Met Val Thr
            100                 105                 110

Val Ser Ser
        115

<210> SEQ ID NO 6
<211> LENGTH: 106
<212> TYPE: PRT
<213> ORGANISM: Artificial Sequence
<220> FEATURE:
<223> OTHER INFORMATION: 42B11G12D3-VL-CBM

<400> SEQUENCE: 6

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30
```

His Trp Phe Gln Gln Lys Pro Gly Lys Ser Pro Lys Leu Leu Ile Tyr
        35                  40                  45

Asp Thr Ser Thr Leu Ala Ser Gly Val Pro Ser Arg Phe Ser Gly Ser
 50                  55                  60

Gly Ser Gly Thr Glu Tyr Thr Leu Thr Ile Ser Ser Met Gln Pro Glu
 65                  70                  75                  80

Asp Phe Ala Thr Tyr Tyr Cys Gln Gln Arg Thr Thr Tyr Pro Leu Thr
                 85                  90                  95

Phe Gly Gln Gly Thr Lys Leu Glu Ile Lys
            100                 105

<210> SEQ ID NO 7
<211> LENGTH: 115
<212> TYPE: PRT
<213> ORGANISM: Artificial Sequence
<220> FEATURE:
<223> OTHER INFORMATION: 42B11G12D3-VH-5BM

<400> SEQUENCE: 7

Gln Val His Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Ile Asn Trp Ile Lys Gln Ala Pro Gly Gln Gly Leu Glu Trp Ile
            35                  40                  45

Gly Arg Ile Ala Pro Gly Ser Gly Thr Thr Tyr Tyr Asn Glu Met Phe
 50                  55                  60

Thr Gly Arg Val Thr Met Thr Val Val Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Phe Asp Tyr Trp Asp Gln Gly Thr Met Val Thr
            100                 105                 110

Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: 42B11G12D3-VL-5BM

<400> SEQUENCE: 8

Asp Ile Val Leu Thr Gln Ser Pro Ser Phe Leu Ser Ala Ser Val Gly
 1               5                  10                  15

Asp Arg Val Thr Ile Thr Cys Ser Ala Ser Lys Ser Val Ser Tyr Ile
                 20                  25                  30

His Trp Tyr Gln Gln Lys Pro Gly Lys Ala Pro Lys Leu Leu Ile Tyr
            35                  40                  45

Asp Thr Ser Thr Leu Ala Ser Gly Val Pro Pro Arg Phe Ser Gly Ser
 50                  55                  60

Gly Ser Gly Pro Ser Tyr Ser Leu Thr Ile Ser Ser Leu Gln Pro Glu
 65                  70                  75                  80

Asp Phe Ala Thr Tyr Tyr Cys Gln Gln Arg Thr Thr Tyr Pro Leu Thr
                 85                  90                  95

Phe Gly Gly Gly Thr Lys Leu Glu Ile Lys
            100                 105

-continued

```
                  100                 105

<210> SEQ ID NO 9
<211> LENGTH: 115
<212> TYPE: PRT
<213> ORGANISM: Artificial Sequence
<220> FEATURE:
<223> OTHER INFORMATION: AH01653-VH

<400> SEQUENCE: 9

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Lys Gln Ala Pro Gly Gln Gly Leu Glu Trp Met
            35                  40                  45

Gly Arg Ile Ala Pro Gly Ser Gly Thr Thr Tyr Tyr Asn Glu Met Phe
        50                  55                  60

Thr Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Phe Asp Tyr Trp Asp Gln Gly Thr Met Val Thr
                100                 105                 110

Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: AH01672-VH

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Lys Gln Ala Pro Gly Gln Gly Leu Glu Trp Met
            35                  40                  45

Gly Arg Ile Ala Pro Gly Ser Gly Thr Thr Tyr Tyr Asn Glu Met Phe
        50                  55                  60

Thr Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Phe Asp Tyr Trp Asp Gln Gly Thr Met Val Thr
                100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: AH01674-VH

<400> SEQUENCE: 11
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
            35                  40                  45

Gly Arg Ile Ala Pro Gly Ser Gly Thr Thr Tyr Tyr Asn Glu Met Phe
        50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Phe Asp Tyr Trp Gly Gln Gly Thr Met Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: AH01679-VH

<400> SEQUENCE: 12

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
            35                  40                  45

Gly Arg Ile Ala Pro Gly Ser Gly Thr Thr Tyr Tyr Asn Glu Met Phe
        50                  55                  60

Thr Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Phe Asp Tyr Trp Gly Gln Gly Thr Met Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: AH01686-VH

<400> SEQUENCE: 13

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Lys Gln Ala Pro Gly Gln Gly Leu Glu Trp Ile
            35                  40                  45

Gly Arg Ile Ala Pro Gly Ser Gly Thr Thr Tyr Tyr Asn Glu Met Phe
```

```
                  50                  55                  60
Thr Gly Arg Val Thr Leu Thr Arg Asp Thr Ser Thr Ser Thr Ala Tyr
 65                  70                  75                  80

Ile Glu Leu Ser Ser Leu Arg Ser Glu Asp Thr Ala Val Tyr Phe Cys
                     85                  90                  95

Ala Arg Gly Asp Tyr Phe Asp Tyr Trp Gly Gln Gly Thr Met Val Thr
                    100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: AH01695-VH

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
             35                  40                  45

Gly Arg Ile Ala Pro Gly Ser Gly Thr Thr Tyr Tyr Asn Glu Met Phe
 50                  55                  60

Thr Gly Arg Val Thr Leu Thr Arg Asp Thr Ser Thr Ser Thr Ala Tyr
 65                  70                  75                  80

Ile Glu Leu Ser Ser Leu Arg Ser Glu Asp Thr Ala Val Tyr Phe Cys
                     85                  90                  95

Ala Ile Gly Asp Tyr Phe Asp Tyr Trp Gly Gln Gly Thr Met Val Thr
                    100                 105                 110

Val Ser Ser
        115

<210> SEQ ID NO 15
<211> LENGTH: 114
<212> TYPE: PRT
<213> ORGANISM: Artificial Sequence
<220> FEATURE:
<223> OTHER INFORMATION: AH01696-VH

<400> SEQUENCE: 15

Val Gln Leu Val Gln Ser Gly Ala Glu Val Lys Pro Gly Ala Ser
 1               5                  10                  15

Val Lys Val Ser Cys Lys Ala Ser Gly Tyr Thr Phe Thr Ser Tyr Trp
                20                  25                  30

Ile Asn Trp Ile Arg Gln Ala Pro Gly Gln Gly Leu Glu Trp Ile Gly
             35                  40                  45

Arg Ile Ala Pro Gly Ser Gly Thr Thr Tyr Tyr Asn Glu Met Phe Thr
 50                  55                  60

Gly Arg Val Thr Leu Thr Arg Asp Thr Ser Thr Ser Thr Ala Tyr Met
 65                  70                  75                  80

Glu Leu Ser Ser Leu Arg Ser Glu Asp Thr Ala Val Tyr Tyr Cys Ala
                     85                  90                  95

Arg Gly Asp Tyr Phe Asp Tyr Trp Gly Gln Gly Thr Met Val Thr Val
                    100                 105                 110
```

-continued

Ser Ser

<210> SEQ ID NO 16
<211> LENGTH: 115
<212> TYPE: PRT
<213> ORGANISM: Artificial Sequence
<220> FEATURE:
<223> OTHER INFORMATION: AH01704-VH

<400> SEQUENCE: 16

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Lys Gln Ala Pro Gly Gln Gly Leu Glu Trp Met
        35                  40                  45

Gly Arg Ile Ala Pro Gly Ser Gly Thr Thr Tyr Tyr Asn Glu Met Phe
    50                  55                  60

Thr Gly Arg Val Thr Leu Thr Arg Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asp Tyr Phe Asp Tyr Trp Gly Gln Gly Thr Met Val Thr
            100                 105                 110

Val Ser Ser
        115

<210> SEQ ID NO 17
<211> LENGTH: 106
<212> TYPE: PRT
<213> ORGANISM: Artificial Sequence
<220> FEATURE:
<223> OTHER INFORMATION: AH01653-VL

<400> SEQUENCE: 17

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Pro Glu Tyr Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gly Gly Thr Lys Leu Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: AH01672-VL

<400> SEQUENCE: 18

Asp Ile Gln Leu Thr Gln Ser Pro Ser Phe Leu Ser Ala Ser Val Gly
1               5                   10                  15

```
Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
            35                  40                  45

Asp Thr Ser Thr Leu Ala Ser Gly Val Pro Pro Arg Phe Ser Gly Ser
        50                  55                  60

Gly Ser Gly Pro Glu Phe Ser Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                    85                  90                  95

Phe Gly Gly Gly Thr Lys Leu Glu Ile Lys
            100                 105
```

<210> SEQ ID NO 19
<211> LENGTH: 106
<212> TYPE: PRT
<213> ORGANISM: Artificial Sequence
<220> FEATURE:
<223> OTHER INFORMATION: AH01674-VL

<400> SEQUENCE: 19

```
Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
            35                  40                  45

Asp Thr Ser Thr Leu Ala Ser Gly Val Pro Pro Arg Phe Ser Gly Ser
        50                  55                  60

Gly Ser Gly Pro Glu Phe Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                    85                  90                  95

Phe Gly Gln Gly Thr Lys Leu Glu Ile Lys
            100                 105
```

<210> SEQ ID NO 20
<211> LENGTH: 106
<212> TYPE: PRT
<213> ORGANISM: Artificial Sequence
<220> FEATURE:
<223> OTHER INFORMATION: AH01679-VL

<400> SEQUENCE: 20

```
Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
            35                  40                  45

Asp Thr Ser Thr Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                    85                  90                  95

Phe Gly Gln Gly Thr Lys Leu Glu Ile Lys
```

100                 105

<210> SEQ ID NO 21
<211> LENGTH: 106
<212> TYPE: PRT
<213> ORGANISM: Artificial Sequence
<220> FEATURE:
<223> OTHER INFORMATION: AH01686-VL

<400> SEQUENCE: 21

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gln Gly Thr Lys Leu Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: AH01695-VL

<400> SEQUENCE: 22

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
        35                  40                  45

Asp Thr Ser Thr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gln Gly Thr Lys Leu Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: AH01696-VL

<400> SEQUENCE: 23

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Phe Gln Gln Lys Pro Gly Lys Ala Pro Lys Leu Leu Ile Tyr
            35                  40                  45

Asp Thr Ser Thr Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gln Gly Thr Lys Leu Glu Ile Lys
                100                 105

<210> SEQ ID NO 24
<211> LENGTH: 106
<212> TYPE: PRT
<213> ORGANISM: Artificial Sequence
<220> FEATURE:
<223> OTHER INFORMATION: AH01704-VL

<400> SEQUENCE: 24

Asp Ile Gln Leu Thr Gln Ser Pro Ser Phe Leu Ser Ala Ser Val Gly
1               5                   10                  15

Asp Arg Val Thr Ile Thr Cys Ser Ala Ser Lys Ser Val Ser Tyr Ile
            20                  25                  30

His Trp Tyr Gln Gln Lys Pro Gly Lys Ala Pro Lys Leu Leu Ile Tyr
            35                  40                  45

Asp Thr Ser Thr Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Thr Thr Tyr Pro Leu Thr
                85                  90                  95

Phe Gly Gln Gly Thr Lys Leu Glu Ile Lys
                100                 105

<210> SEQ ID NO 25
<211> LENGTH: 5
<212> TYPE: PRT
<213> ORGANISM: Artificial Sequence
<220> FEATURE:
<223> OTHER INFORMATION: HCDR1

<400> SEQUENCE: 25

Ser Tyr Trp Ile Asn
1               5

<210> SEQ ID NO 26
<211> LENGTH: 17
<212> TYPE: PRT
<213> ORGANISM: Artificial Sequence
<220> FEATURE:
<223> OTHER INFORMATION: HCDR2

<400> SEQUENCE: 26

Arg Ile Ala Pro Gly Ser Gly Thr Thr Tyr Tyr Asn Glu Met Phe Thr
1               5                   10                  15

Gly

<210> SEQ ID NO 27
<211> LENGTH: 6
<212> TYPE: PRT

```
<213> ORGANISM: Artificial Sequence
<220> FEATURE:
<223> OTHER INFORMATION: HCDR3

<400> SEQUENCE: 27

Gly Asp Tyr Phe Asp Tyr
1               5

<210> SEQ ID NO 28
<211> LENGTH: 10
<212> TYPE: PRT
<213> ORGANISM: Artificial Sequence
<220> FEATURE:
<223> OTHER INFORMATION: LCDR1

<400> SEQUENCE: 28

Ser Ala Ser Lys Ser Val Ser Tyr Ile His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: LCDR2

<400> SEQUENCE: 29

Asp Thr Ser Thr Leu Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: LCDR3

<400> SEQUENCE: 30

Gln Gln Arg Thr Thr Tyr Pro Leu Thr
1               5

<210> SEQ ID NO 31
<211> LENGTH: 11
<212> TYPE: PRT
<213> ORGANISM: Artificial Sequence
<220> FEATURE:
<223> OTHER INFORMATION: chimeric antibody control

<400> SEQUENCE: 31

Tyr Asn Glu Met Phe Thr Gly Lys Ala Thr Leu
1               5                   10

<210> SEQ ID NO 32
<211> LENGTH: 8
<212> TYPE: PRT
<213> ORGANISM: Artificial Sequence
<220> FEATURE:
<223> OTHER INFORMATION: AH01674

<400> SEQUENCE: 32

Tyr Asn Glu Met Phe Thr Gly Arg
1               5

<210> SEQ ID NO 33
<211> LENGTH: 11
<212> TYPE: PRT
<213> ORGANISM: Artificial Sequence
```

```
<220> FEATURE:
<223> OTHER INFORMATION: AH01695-1

<400> SEQUENCE: 33

Tyr Asn Glu Met Phe Thr Gly Arg Val Thr Leu
1               5                   10

<210> SEQ ID NO 34
<211> LENGTH: 11
<212> TYPE: PRT
<213> ORGANISM: Artificial Sequence
<220> FEATURE:
<223> OTHER INFORMATION: AH01695-2

<400> SEQUENCE: 34

Tyr Asn Glu Met Phe Thr Gly Arg Val Thr Leu
1               5                   10
```